United States Patent [19]
Atassi et al.

[11] Patent Number: 5,578,496
[45] Date of Patent: Nov. 26, 1996

[54] DETECTION OF AUTOANTIBODIES ASSOCIATED WITH THE DISEASE MYASTHENIA GRAVIS

[75] Inventors: M. Zouhair Atassi; Tetsuo Ashizawa, both of Houston, Tex.

[73] Assignee: Board of Regents, Baylor College of Medicine, Houston, Tex.

[21] Appl. No.: 318,200

[22] Filed: Oct. 5, 1994

Related U.S. Application Data

[63] Continuation of Ser. No. 965,670, Oct. 20, 1992, abandoned, which is a continuation-in-part of Ser. No. 811,050, Dec. 19, 1991, abandoned.

[51] Int. Cl.$^6$ .................... G01N 33/564; G01N 33/53; A61K 38/00; C07K 5/00
[52] U.S. Cl. .................... 436/506; 435/7.92; 530/326; 424/184.1; 424/185.1
[58] Field of Search .................... 435/7.1; 436/506, 436/507, 518, 542, 514; 530/326

[56] References Cited

U.S. PATENT DOCUMENTS 5,041,389  8/1991  Lindstrom .................... 436/518

FOREIGN PATENT DOCUMENTS

| | | |
|---|---|---|
| 85306855 | 9/1985 | European Pat. Off. . |
| 89107960 | 3/1989 | European Pat. Off. . |
| 89105728 | 3/1989 | European Pat. Off. . |
| PCTUS9002144 | 4/1990 | European Pat. Off. . |
| 90109907 | 5/1990 | European Pat. Off. . |
| 60-078996 | 5/1985 | Japan .................... C07K 7/00 |
| 1469472 | 7/1973 | United Kingdom . |

OTHER PUBLICATIONS

Ashizawa et al., 1992, Profile of the regions on the α–chain of human acetylcholine receptor recognized by autoantibodies in myasthenia gravis, Molec. Immunol., 29:15077–1514.
Oshima et al., 1990, Autoimmune T–cell recognition of human acetylcholine receptor: the sites of T–cell recognition in myasthenia gravis on the extracellular part of the α subunit, Eur. J. Immunol., 20:2563–2589.
Tzartos et al., 1988, Localization of the main immunogenic region of human muscle acetylcholine receptor to residues 67–76 of the α subunit, Proc. Natl. Acad. Sci., USA, 85:2899–2903.
Lennon and Griesmann, 1989, Evidence against acetylcholine receptor having a main immunogenic region as a target for autoantibodies in myasthenia gravis, Neurol., 39:1069–1076.

Sano et al., 1991, Identification of three extended antibody-–binding segments in recombinant human muscle acetylcholine receptor α subunit extracellular domain 1–210, Internatl. Immunol., 3:983–989.
Mulac–Jericevic et al., 1987, Profile of the continuous antigenic regions on the extracellular part of the α chain of an aceylcholine receptor, Proc. Natl. Acad. Sci., USA, 84:3633–3637.
Ashizawa, T. et al. (1991) Adv. Exp. Med. Biol. 303:255–261.
Kazim, A. L. et al. (1980) Biochem. J. 191:261–264.
Kazim, A. L. et al. (1982) Biochem. J. 203:201–208.
Mulac–Jericevic, B. et al. (1987) Proc. Natl. Acad Sci USA 84:3633–3637.
Howlfeld, R. et al. (1988) J. Clin. Invest. 81:657–660.
Oshima, M. et al. (1990) Eur. J. Immunol. 20:2563–2569.
Mulac–Jericevic, B. et al. (1988) J. Prot. Chem. 7:173–177.
Suppression of Reaginic Antibodies with Modified Allergens, "III. Preparation of Tolerogenic Conjugates of common Allergens with Monomethoxypolyethylene Glycols of Different Molecular Weights by the Mixed Anhydride Method," by S. I. Wie, C. W. Wie, W. Y. Lee, L. G. Filion, A. H. Sehon and E. Akerblom, International Archives of Allergy and Applied Immunology, vol. 64 (1981).

(List continued on next page.)

Primary Examiner—Robert D. Budens
Assistant Examiner—Heffrey S. Parkin
Attorney, Agent, or Firm—C. Steven McDaniel

[57] ABSTRACT

This invention is directed towards peptidic compositions, methods, and diagnostic kits for the accurate and sensitive detection of human acetylcholine receptor (AChR) autoantibodies associated with the disease myasthenia gravis (MG). Eighteen synthetic overlapping oligopeptides encompassing the entire extracellular domain (residues α1-210) of the α-chain of human AChR and an additional peptide (residues α262-276) corresponding to the extracellular connection between the two transmembrane regions were prepared. The immunologic reactivity of these peptides against autoantibodies in the plasma of patients with MG was ascertained by solid-phase radioimmunoassay. Autoantibody responses were subjected to genetic regulation as indicated by the variation in recognition profiles from patient to patient. However, it was possible to detect AChR autoantibodies in a heterogenous patient population by employing a peptide mixture comprising at least four peptides (SEQ ID NOS. 8, 17, 18, and 23). These peptides correspond to the following regions of the AChR: α12-27, α111-126, α122-138, and α182-198. These reagents provide a peptide-based direct antibody binding method for the detection of myasthenogenic autoantibodies.

11 Claims, 16 Drawing Sheets

OTHER PUBLICATIONS

Suppression of Reaginic Antibodies with Modified Allergens, "III. Down-regulation of secondary in vitro antibody responses by suppressor T cells of mice treated with a tolerogenic conjugate of ovalbumin and monomethoxypolyethylene glycol, OVA(mPEG)$_{13}$", by S. suppressor T cells of mice treated with a tolerogenic conjugate of ovalbumin and monometoxypolyethylene glycol, OVA(mPEG)$_{13}$, by S. Mokashi, V. Holford–Strevens, G. Sterrantino, C. J. C. Jackson and A. H. Sehon, Immunology Letters, 23 (1989/1990) 95–102.

Preparation and Immunochemical Properties of Methoxypolyethylene Glycol-Coupled and N-Carboxymethylted Derivatives of Ragweed Pollen Allergen, Antigen E[1], by TePiao King, Loucia Kochoumian, and Lawrence M. Lichtenstein, Archives of Biochemistry and Biophysics, Lawrence M. vol. 178, pp. 442–450 (1977).

Abrogation of reaginic antibodies with modified allergens, by Weng Y. Lee and Alec H. Sehon, Nature, vol. 267, pp. 618–619, Jun. 16, 1977.

Suppression of Reagini Antibodies with Modified Allergens, "IV. Induction of Suppressor T Cells by Conjugates of Polyethylene Glycol (PEG) and Monomethoxy PEG with Ovalbumin," by W. Y. Lee, A. H. Sehon and E. Akerblom, International Archives of Allergy and Applied Immunology, vol. 64, pp. 100–114 (1981).

Suppression of Reaginic Antibodies with Modified Allergens, "I. Reduction in Allergenicity of Protein Allergens by Conjugation to Polyethylene Glycol," by Weng . Lee and Alec H. Sehon, International Archives of Allergy and Applied Immunology, vol. 56, pp. 159–170.

Suppression of Reaginic Antibodies with Modified Allergens, "II. Abrogation of Reaginic Antibodies with Allergens Conjugated to Polyethylene Glycol," by Weng Y. Lee and Alec H. Sehon, International Archives of Allergy and Applied Immunology, vol. 56, pp. 193–206 (1978).

"Hyposensitization in asthmatics with mPEG–modified and unmodified house dust mite extract, IV. Occurrence and prediction of side effects," by H. Mosbech, A. Dirksen, S. Dreborg, L. Frolund, J. H. Heining, U. G. Svendsen, M. Soborg, E. Taudorf & B. Weeke, Allergy, No. 45, pp. 142–150 (1990).

Modulation of Antibody Responses by Conjugates of Antigens With Monomethoxypolyethylene Glycol, by Alec H. Sehon, Immunobiology of Proteins and Peptides V Vaccines, pp. 341–351.

New Model Visual Pigments, Spectroscopy of Poly(ethylene glycol) Peptide Schiff bases of Retinal, by P. K. Das, Ralph S. Becker, Dieter Hannak, and Ernst Bayer, Journal of the American Chemical Society, vol. 101, No. 1, Jan. 3, 1979, pp. 239–240.

Soluble Polymers in Organic Syntheses: II. Use of Polyethylene Glycol–Bound Reagents for Peptide Syntheses, by Manfred Mutter, Tetrahedron Letters, No. 31, Jul. 1978. pp. 2842–2846.

Syntheses of Poly(ethylene Glycol)–Bound NADP by Selective Modification at the 6–amino group of NADP, by Keiko Okuda, Itaru Urabe, and Hirosuke Okada, European Journal of Biochemistry, vol., 151, No. 1, Aug. 11, 1985. pp. 33–38.

A Poly(oxyethylene)–Supported Cys–Pro–Leu–Cys/Fe(II) Complex as a Rubredoxin Model: Protection of the Fe–Cys Coordination from Hydrolysis in Aqueous Solution, by Norikazu Ueyama, Michio Nakata, and Akira Nakamura, Polymer Journal, vol. 17, No. 5, pp. 721–727 (1985).

Development of new Functionalized Polymers and Their Utilization in Peptide Chemistry, by Shmuel Zalipsky, Ph.D., University of Minnesota (1987), Dissertation Abstracts International (The Sciences and Engineering), vol. 48, No. 8 (Feb. 1988).

Engineering Proteins to Enhance Their Partition Coefficients in Aqueous Two–Phase Systems, by Kristina Kohler, Charlotta Ljungquist Akihiko Kondo, Andres Veide, and Bjorn Nilsson, Biotechnology, vol. 9, No. 7, Jul. 1991. pp. 642–646.

Preparation of Polyethylene Glycol Derivatives with two Different Functional groups at the Termini, by Shmuel Zalipsky and George Barany, Polymer Preprints, vol. 27, No. 1, Apr. 1986. pp. 1–2.

Investigation into the Spectroscopy and Photoisomerization of a Series of Ploy(Ethylene Glycol) peptide Schiff Bases of 11–cis Retinal, by Kenn Freedman, Ralph S. Becker, Dieter Hannak, and Ernst Bayer, Photochemistry and Photobiology, vol. 43, No. 3, Mar. 1986. pp. 291–295.

Clinical trial of Stealth Doxorubicin Initiated (Ability to Evade the Body's Immune System "Radar"), AIDS Weekly, p. 4, May 27, 1991.

Modification of Batroxobin with Activated Polyethylene Glycol: Reduction of Binding Ability Towards Anti–Batroxobin Antibody and Retention of Defibrinogenation Activity in Circulation of Preimmun–Dogs, by Hiroyuki Nushimura, Katsunobu Takahashi, Katsukiyo Sakurai Kazunobu Fujinuma, Yasushi Imamura, Mitsuoki Ooba, and Yuji Inada, Life Sciences, vol. 33, No. 15, Oct. 10, 1983. pp. 1467–1473.

A Double–Blind Study Comparing Monomethoxy Polyethylene Glycol–Modified Honeybee Venom and Unmodified Honeybee Venom for Immunotherapy, by Ulrich Muller, M. D., Arthur R. Rabson, M. R. C. Path., Marium Bischof, M. D.,Ruth Lomnitzer, Ph.D., Sten Dreborg, M. D., and Ake Lanner, M.Sc., The Journal of Allergy and Clinical Immunology, vol. 80, No. 1 (1987). pp. 252–261.

Synthesis, Isolation, and Characterization of Conjugates of Ovalbumin with Monomethoxypolyethylene Glycol Using Cyanuric Chloride as the Coupling Agent, by Chung–Ja C. Jackson, James L. Charlton, Kimberly Kuzminski, Glen M. Lang, and Alex H. Sehon, Analytical Biochemistry, vol. 165, pp. 114–127 (1987).

A convenient general Method for synthesis of $N_\alpha$ or $N^\omega$ Dithiasuccinoyl (Dts) Amino Acids and Dipeptides: Application of Polyethylene Glycol as a Carrier for Functional Purification, by Shumuel Zalipsky, Fernando Albericio, Utaszula Slomczynska, and George Barany. pp. 740–783.

Characterization of a Polyethylene Glycol Conjugate of Recombinant Human Interferon, by Kita Yoshiko, Michael F. Rohde, Rsutomu Arakawa, Katerina D. Fagin, Eleanor N. Fish, and Kris Benerjee, Drug Design and Delivery, vol. 6, pp. 157–167 (1990).

Soluble Polymers in Organic Syntheses 3. Polyethylene Glycol as Acid Labile Solubilizing Protecting Group, by h. Anzinger and M. Mutter, Polymer Bulletin, No. 66, Nov. 22, 1982.

Enzyme Modification by MPEG with an Amino Acid or Peptide as Spacer Arms, by Luciana Sartore, Paolo Caliceti, Oddone Schiavon, and Francesco M. Veronese, Applied Biochemistry and Biotechnology, vol. 27, No. 1, Jan. 1991.

1. Gly.Lys.Val.Tyr.Leu.Val.Gly.Gly.Pro.Glu.Leu.Gly.Gly.Trp.Lys

2. Glu.Val.Trp.Arg.Glu.Glu.Ala.Tyr.His.Ala.Cys.Asp.Ile.Lys.Asp

3. Pro.Gly.Gly.Pro.Asp.Arg.Phe.Thr.Leu.Leu.Thr.Pro.Gly.Ser.His

4. Thr.Pro.Gly.Ser.His.Phe.Ile.Cys.Thr.Lys.Asp.Gln Lys.Phe.Val

5.         H₂N-Lys.Ser.Tyr.Cys.Glu.Ile.Ile.Val.Thr.His.
                                                  Phe
    HO-Ile.Gly.Leu.Lys.Met.Thr.Cys.Asn.Gln.Gln.Asp.Phe.Pro

6.    H2N-Lys.Ser.Pro.Cys.Ala.Tyr.Lys.Glu.
                      |                    Pro
                 |
   HO-Cys.Ala.Val.Thr.Thr.Glu

FIG. 1

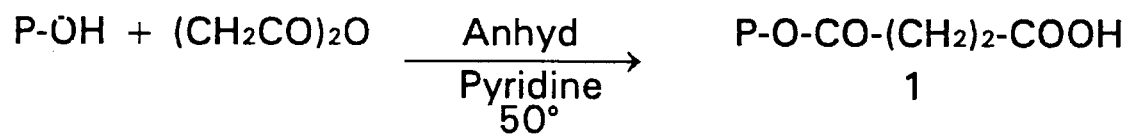
FIG. 2A
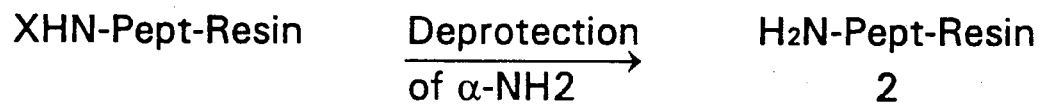
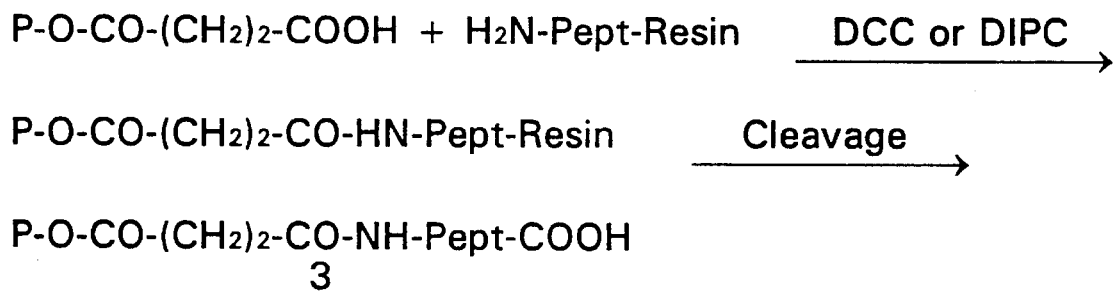
P = tolerogenic polymer (mPEG or PVA)
DCC = dicyclohexylcarbodiimide
DIPC = diisopropylcarbodiimide
X = t-Boc or Fmoc
FIG. 2B

| Peptide Position | Structure |
|---|---|
| α1-16 | S E H E T R L V A K L F K D Y S |
| α12-27 | F K D Y S S V V R P V E D H R Q |
| α23-38 | E D H R Q V V E V T V G L Q L I |
| α34-49 | G L Q L I Q L I N V D E V N Q I |
| α45-60 | E V N Q *I V T T* N V R L K Q Q W |
| α56-71 | L K Q Q W V D Y N L K W N P D D |
| α67-82 | W N P D D Y G G V K K I H I P S |
| α78-93 | I H I P S E K I W R P D L V L Y |
| α89-104 | D L V L Y N N A D G D F A I V K |
| α100-115 | F A I V K F T K V L L Q Y T G H |
| α111-126 | Q Y T G H I T W T P P A I F K S |
| α122-138 | A I F K S Y G E I I V T H F P F D |
| α134-150 | H F P F D E Q N G S M K L G T W T |
| α146-162 | L G T W T Y D G S V V A I N P E S |
| α158-174 | I N P E S D Q P D L S N F M E S G |
| α170-186 | F M E S G E W V I K E S R G W K H |
| α182-198 | R G W K H S V T Y S G G P D T P Y |
| α194-210 | P D T P Y L D I T Y H F V M Q R L |
| | |
| α262-276 | E L I P S T S S A V P L I G K |

FIG. 11

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( x i ) SEQUENCE DESCRIPTION: SEQ ID NO:1:

```
Gly  Lys  Val  Tyr  Leu  Val  Gly  Gly  Pro  Glu  Leu  Gly  Gly  Trp  Lys
1              5                        10                         15
```

( 2 ) INFORMATION FOR SEQ ID NO:2:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( x i ) SEQUENCE DESCRIPTION: SEQ ID NO:2:

```
Glu  Val  Trp  Arg  Glu  Glu  Ala  Trp  His  Ala  Cys  Asp  Ile  Lys  Asp
1              5                        10                         15
```

( 2 ) INFORMATION FOR SEQ ID NO:3:

( i ) SEQUENCE CHARACTERISTICS:

(A) LENGTH: 15 amino acids
(B) TYPE: amino acid
(D) TOPOLOGY: linear (i i) MOLECULE TYPE: peptide (x i) SEQUENCE DESCRIPTION: SEQ ID NO:3:

Pro Gly Gly Pro Asp Arg Phe Thr Leu Leu Thr Pro Gly Ser His
1               5                   10                  15

(2) INFORMATION FOR SEQ ID NO:4:

(i) SEQUENCE CHARACTERISTICS:
    (A) LENGTH: 15 amino acids
    (B) TYPE: amino acid
    (D) TOPOLOGY: linear (i i) MOLECULE TYPE: peptide (x i) SEQUENCE DESCRIPTION: SEQ ID NO:4:

Thr Pro Gly Ser His Phe Ile Cys Thr Lys Asp Gln Lys Phe Val
1               5                   10                  15

(2) INFORMATION FOR SEQ ID NO:5:

(i) SEQUENCE CHARACTERISTICS:
    (A) LENGTH: 24 amino acids
    (B) TYPE: amino acid
    (D) TOPOLOGY: circular (i i) MOLECULE TYPE: peptide (i x) FEATURE:
    (A) NAME/KEY: Disulfide-bond
    (B) LOCATION: 4..18
    (C) OTHER INFORMATION: /note="internal disulfide
        linkages creating peptide loop"

(x i) SEQUENCE DESCRIPTION: SEQ ID NO:5:

Lys Ser Tyr Cys Glu Ile Ile Val Thr His Phe Pro Phe Asp Gln Gln
1               5                   10                  15

Asn Cys Thr Met Lys Leu Gly Ile
20

(2) INFORMATION FOR SEQ ID NO:6:

(i) SEQUENCE CHARACTERISTICS:
    (A) LENGTH: 15 amino acids
    (B) TYPE: amino acid
    (D) TOPOLOGY: circular (i i) MOLECULE TYPE: peptide (i x) FEATURE:
    (A) NAME/KEY: Disulfide-bond
    (B) LOCATION: 4..15
    (C) OTHER INFORMATION: /note="internal disulfide
        linkages creating peptide loop"

(x i) SEQUENCE DESCRIPTION: SEQ ID NO:6:

Lys Ser Pro Cys Ala Tyr Lys Glu Pro Glu Thr Thr Val Ala Cys
1               5                   10                  15

(2) INFORMATION FOR SEQ ID NO:7:

(i) SEQUENCE CHARACTERISTICS:
    (A) LENGTH: 16 amino acids
    (B) TYPE: amino acid
    (D) TOPOLOGY: linear (i i) MOLECULE TYPE: peptide ( x i ) SEQUENCE DESCRIPTION: SEQ ID NO:7:

Ser Glu His Glu Thr Arg Leu Val Ala Lys Leu Phe Lys Asp Tyr Ser
1               5                   10                  15

( 2 ) INFORMATION FOR SEQ ID NO:8:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

Phe Lys Asp Tyr Ser Ser Val Val Arg Pro Val Glu Asp His Arg Gln
1               5                   10                  15

( 2 ) INFORMATION FOR SEQ ID NO:9:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Glu Asp His Arg Gln Val Val Glu Val Thr Val Gly Leu Gln Leu Ile
1               5                   10                  15

( 2 ) INFORMATION FOR SEQ ID NO:10:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

Gly Leu Gln Leu Ile Gln Leu Ile Asn Val Asp Glu Val Asn Gln Ile
1               5                   10                  15

( 2 ) INFORMATION FOR SEQ ID NO:11:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

Glu Val Asn Gln Ile Val Thr Thr Asn Val Arg Leu Lys Gln Gln Trp
1               5                   10                  15

( 2 ) INFORMATION FOR SEQ ID NO:12:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

Leu Lys Gln Gln Trp Val Asp Tyr Asn Leu Lys Trp Asn Pro Asp Asp
1               5                   10                  15

( 2 ) INFORMATION FOR SEQ ID NO:13:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

```
Trp Asn Pro Asp Asp Tyr Gly Gly Val Lys Lys Ile His Ile Pro Ser
1               5                   10                  15
```

( 2 ) INFORMATION FOR SEQ ID NO:14:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

```
Ile His Ile Pro Ser Glu Lys Ile Trp Arg Pro Asp Leu Val Leu Tyr
1               5                   10                  15
```

( 2 ) INFORMATION FOR SEQ ID NO:15:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

```
Asp Leu Val Leu Tyr Asn Asn Ala Asp Gly Asp Phe Ala Ile Val Lys
1               5                   10                  15
```

( 2 ) INFORMATION FOR SEQ ID NO:16:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

```
Phe Ala Ile Val Lys Phe Thr Lys Val Leu Leu Gln Tyr Thr Gly His
1               5                   10                  15
```

( 2 ) INFORMATION FOR SEQ ID NO:17:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

```
Gln Tyr Thr Gly His Ile Thr Trp Thr Pro Pro Ala Ile Phe Lys Ser
1               5                   10                  15
```

( 2 ) INFORMATION FOR SEQ ID NO:18:

( i ) SEQUENCE CHARACTERISTICS:

( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

Ala Ile Phe Lys Ser Tyr Gly Glu Ile Ile Val Thr His Phe Pro Phe Asp
1               5                   10                  15

( 2 ) INFORMATION FOR SEQ ID NO:19:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

His Phe Pro Phe Asp Glu Gln Asn Gly Ser Met Lys Leu Gly Thr Trp Thr
1               5                   10                  15

( 2 ) INFORMATION FOR SEQ ID NO:20:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

Leu Gly Thr Trp Thr Tyr Asp Gly Ser Val Val Ala Ile Asn Pro Glu Ser
1               5                   10                  15

( 2 ) INFORMATION FOR SEQ ID NO:21:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

Ile Asn Pro Glu Ser Asp Gln Pro Asp Leu Ser Asn Phe Met Glu Ser Gly
1               5                   10                  15

( 2 ) INFORMATION FOR SEQ ID NO:22:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

Phe Met Glu Ser Gly Glu Trp Val Ile Lys Glu Ser Arg Gly Trp Lys His
1               5                   10                  15

( 2 ) INFORMATION FOR SEQ ID NO:23:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

Arg Gly Trp Lys His Ser Val Thr Tyr Ser Gly Gly Pro Asp Thr Pro Tyr
1               5                   10                  15

( 2 ) INFORMATION FOR SEQ ID NO:24:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

Pro Asp Thr Pro Tyr Leu Asp Ile Thr Tyr His Phe Val Met Gln Arg Leu
1               5                   10                  15

( 2 ) INFORMATION FOR SEQ ID NO:25:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

Glu Leu Ile Pro Ser Thr Ser Ser Ala Val Pro Leu Ile Gly Lys
1               5                   10                  15

DETECTION OF AUTOANTIBODIES ASSOCIATED WITH THE DISEASE MYASTHENIA GRAVIS

The U.S. Government has a paid-up license in this invention and the right in limited circumstances to require the patent owner to license others on reasonable terms as provided for by the terms of Grant No. NS26280 awarded by the National Institutes of Health.

This is a continuation of application Ser. No. 07/965,670 filed on Oct. 20, 1992, now abandoned, which is a continuation-in-part of Ser. No. 07/811,050 filed on Dec. 19, 1991, now abandoned.

BACKGROUND OF THE INVENTION

A. Field of the Invention

The invention relates, in an initial aspect, to the detection and treatment of an autoimmune disease, myasthenia gravis. Compositions of matter (peptides and combinations of peptides) and methods are disclosed which enable a high degree of predictive capability for detecting this neurological disease. The invention's therapies rely, in the first instance, on compositions and methods which are sensitive enough to allow detection of low levels of the autoantibodies associated with the symptoms of the disease, yet which virtually eliminate false readings. With such sensitive and accurate tests, a physician may confidently proceed to apply the treatments and methods using the therapeutic compositions and methods of the invention.

The invention relates, in another aspect, to procedures for synthesis of well-defined conjugates of peptides covalently bonded to tolerogenic polymers such as monomethoxypolyethylene glycol (mPEG) or polyvinyl alcohol (PVA). The first step in said synthesis involves succinylation of free-hydroxyl groups on the tolerogenic polymer by reaction with succinic anhydride. The polymer is then coupled to one or the other terminus, for instance via the carboxyl of a succinyl group to the $\alpha$-$NH_2$, of a peptide. This is achieved while maintaining intact all the side-chain protecting groups on the peptide. The MPEG or PVA-peptide conjugates are cleaved from a synthetic resin and purified. This method results in the preparation of conjugates in which one molecule of tolerogenic polymer is specifically coupled to one or the other or both of the termini of an otherwise unaltered peptide molecule.

In order to test the ability of such tolerogenic peptides to suppress antibody responses in an autoimmune disease, a synthetic peptide, $\alpha$125-148, corresponding to a myasthenogenic region of *Torpedo californica* acetylcholine receptor (AChR) was conjugated to monomethoxypolyethylene glycol (MPEG). Injection of mice with the MPEG-($\alpha$125-148) conjugate and subsequent immunization with whole Torpedo AChR suppressed the development of experimental autoimmune myasthenia gravis (EAMG or MG) by electrophysiological criteria. In anti-AChR antisera from these animals, the antibody response against the unconjugated peptide $\alpha$125-148 was decreased while the antibody responses against whole AChR and other epitopes were not altered. There were no detectable changes in T cell proliferation responses to peptide $\alpha$125-148 or to whole AChR in these animals. Prior injections with a "nonsense" peptide mPEG conjugate had no effect on responses to the subsequent immunization with whole Torpedo AChR. The results indicate that the mPEG-($\alpha$125-148) conjugate has epitope-specific tolerogenicity for antibody responses in EAMG, and that the region $\alpha$125-148 plays an important pathophysiological role in EAMG. These studies strongly indicate that other epitope-directed tolerogenic conjugates will be useful for future immunotherapies of human myasthenia gravis.

By way of further example, tolerogenic peptides are also disclosed for diseases as diverse as ragweed pollen allergy and Grave's disease. The strategy of specific suppression of the antibody response to a pre-determined epitope using a synthetic mPEG-peptide conjugate will be useful in manipulation and suppression of unwanted immune responses such as autoimmunity and allergy.

B. Specific Background

SPECIFIC BACKGROUND RELATING TO ACETYLCHOLINE RECEPTOR

The nicotinic acetylcholine receptor (AChR) plays a central role in post-synaptic neuromuscular transmission by mediating ion flux across the cell membrane in response to binding of acetylcholine (Karlin, 1980; Changeux et al. 1984; Hucho, 1986). Myasthenia gravis (MG) is a disabling autoimmune disease in which autoantibodies are produced against AChR and inhibit its regulatory activity. The receptor is a pentamer composed of four subunits ($\alpha_2\beta\delta$). Functional studies have focused mostly on the $\alpha$-subunit because it has been shown to be responsible for binding acetylcholine (Moore and Raftery, 1979; Sobel et al. 1977; Tzartos and Changeux, 1983; McCormick and Atassi, 1984) and $\alpha$-neurotoxins (Lee, 1979). The primary structure of the human $\alpha$-subunit has been reported (Noda et al. 1983). From the primary structure of each subunit, it was possible to identify transmembrane hydrophobic regions and the extracellular part of the chain (Guy, 1984; Finer-Moore and Stroud, 1984; Noda et al. 1983). Immunological and toxin-binding studies (Atassi et al. 1988) to inter-transmembrane synthetic peptides confirmed the model postulating five transmembrane regions (Guy, 1984; Finer-Moore and Stroud, 1984).

Kazim and Atassi (1980) introduced a comprehensive synthetic approach that was specifically designed to localize the full profile of the continuous regions of antibody and T-cell recognition (as well as other recognition regions) on a protein molecule. This approach consisted of the examination of the activities of consecutive synthetic overlapping peptides, of uniform size and overlaps, that encompass the entire protein chain (Kazim and Atassi, 1980; Kazim and Atassi, 1982). This strategy has been applied (Mulac-Jericevic et al. 1987) to the $\alpha$-chain of *Torpedo californica* AChR to localize the continuous regions recognized by mouse and rabbit anti-AChR antibodies, as well as regions concerned with other activities (Atassi et al. 1987).

Presently, one of the tests frequently used to diagnose MG relies on a radio immunoassay (RIA) for anti-AChR autoantibodies in human sera. Only traces of human AChR in crude preparations are obtainable from muscle extracts and therefore directly labeled AChR cannot be used for RIA. The muscle extract is allowed to bind $^{125}$I-labeled $\alpha$-bungarotoxin (BgTX) and the $^{125}$I-labeled BgTX-AChR complex is used for assay of the autoantibodies (Lindstrom et al. 1976; Lefvert et al. 1978; Oger et al. 1987). It has been shown, however, that sera of MG patients contain autoantibodies which compete with BgTX for the binding sites of AChR (Falpius et al. 1980), particularly when these sera are used in excess (Vincent and Newson-Davis, 1985). Therefore, this method often yields very low or false negatives (for examples of such erroneous results, see samples 3, 11, 12 and 15, Table 2).

SPECIFIC BACKGROUND RELATING TO OTHER IMMUNE DISEASE

Other autoimmune diseases and other undesirable immune responses such as allergic responses have been investigated sufficiently well to identify similar specific epitopes which may be the principal causative agent in the disease. Thus, for instance, ragweed pollen allergy is a condition resulting from IgE responses to ragweed allergens such as antigen E, antigen K and Ra3. Thus, it is known from the work of the present inventors that one can map the IgG and IgE antibody and the T-cell epitopes of Ra3 (Atassi and Atassi, 1985, 1986; Kurasaki et al. 1986). Animal models (rat) exist which are used to study the allergic responses.

Similarly, Grave's disease is an autoimmune disease caused by antibody and T-cell responses to epitopes on thyroid-stimulating receptor (TSHR). Recently, the hormone-binding regions on TSHR were localized (Atassi, et al. 1991). As is known due to recent press coverage, both human (President and Mrs. George Bush) and animal (the family pet dog of the President and First Lady) forms of this disease are known.

SPECIFIC BACKGROUND RELATING TO IMMUNOSUPPRESSIVE THERAPY

Some of the earliest methods combining the use of amino acid synthesis with polymers such as polyethylene glycol (PEG) were as resins for the synthesis of peptides. These methods relate generally to attachment of PEG at the carboxy terminus of the growing peptide chain. Typically, the resulting synthetic peptide is ultimately cleaved from the PEG resin and purified. For instance, Anzinger and Mutter (1982), relates to modified PEG moieties capable of binding both C- and N-termini of synthetic peptides for purposes as a soluble carrier and as a solubilizing protecting group in peptide syntheses.

Alternatively, tolerogenic polymers have been used to derivatize proteins and peptides in a permanent, covalent fashion. Prior research has shown that mPEG-protein conjugates may be constructed by non-selective coupling of the polymer to proteins, usually via the ε-amino groups of lysine residues on the surfaces of such proteins. Such substitutions result in multiple derivatives.

Previous studies, for instance, have shown that conjugation of polyethylene glycol, monomethoxypolyethylene glycol (MPEG) or polyvinyl alcohol (PVA) with various protein antigens causes a loss of most of the antigenicity of the native antigens (Abuchowski et al., 1977; Lee and Sehon 1977, 1978a; King et al., 1977, 1979; Davis et al., 1980; Sehon and Lang, 1986). It has also been demonstrated that prior injection of animals with antigen-mPEG conjugates leads to the development of tolerance to subsequent immunization with the native antigen (Lee and Sehon 1977, 1978b; King et al., 1979).

mPEG-derivatization has been used to produce whole-protein and protein fraction conjugates. Abuchowski et al. (1977) relates, for instance to the derivatization of bovine serum albumin with mPEG causing this molecule to become essentially non-immunogenic. Lee and Sehon (1977) similarly converted ovalbumin and mixtures of non-dialyzable allergenic constituents of the aqueous extract of ragweed pollen. King et al. (1979) relates to the comparative study of different tolerogenic polymers indiscriminately conjugated with ragweed antigen E. Nishimura, et al. (1983), relates to the use of an indiscriminately PEG-derivatized snake venom with a molecular weight of 36,000. British Patent 1 469 472 appears to relate to the desire to enable polypeptides such as insulin a longer residence time in the circulatory system and a lessened allergic reaction by indiscriminate conjugation of such polypeptides to PEG.

In certain cases, the indiscriminate conjugation of polymer to protein has been controlled to a limited extent. For instance, European Patent Application 0,335,423 relates to the hG-CSF polypeptide derivatized with a PEG moiety. The derivatization appears to be indiscriminate even though the disclosure does provide for as few as a single PEG molecule per molecule of hG-CSF by controlling the stoichiometric ratios of the polymer to protein. Kita, et al. (1990), relates to the selective modification of one of three (including the N-terminal) residues within human interferon in order to obtain active interferon from recombinant bacteria. The PEG modification was seen to increase the serum half-life of the interferon without substantial decrease in its biological efficacy.

Tolerogenic polymers have also been used to derivatize certain peptides. In the past, modifying peptides with PEG generally required use of methods for activation including: (1) activation with triazine derivatives of PEG; (2) activation of PEG using the active ester method with N-hydroxylsuccinimide; (3) activation of PEG with carbonyldiimidazole; (4) activation of PEG with aldehydes; and so on. These modification methods involved modifying the amino groups at the N-terminal or in the side chain of the lysine residues of the peptides. For instance, Becker and Bayer (1979), relates to synthetic peptides with PEG conjugated to $NH_2$ groups which are available for coupling. In certain cases, where the only reactive $NH_2$ group in the peptide is the α-$NH_2$, the PEG molecule was conjugated to the N-terminus of the peptide. Such methodology, however, relied on the fact that no other reactive amine groups existed in the peptide to be derivatized.

In some instances, peptides have been derivatized using distinct chemical moieties apart from the N-terminus amino group: Ueyama, et al. (1985), relates to the conjugation of PEG to cysteine-containing peptides through the carboxy groups in said cysteines. European Patent Applications 0,340,741 and 0,400,486 relate to PEG derivatives for use as a peptide (particularly protein)-modifying reagent in peptides having guanidino groups. PCT International Application, Pub. No. 90/12874, relates to the modification of polypeptides such as IL, G-CSF or EPO by non-N-terminal conjugation of PEG to cysteine residues in such polypeptides. Sartore, et al. (1991), relates to a method of producing a reagent comprising mPEG attached to an amino acid or a peptide, the amino acid or peptide functioning as a traceable spacer arm between the reagent and a derivatizable polypeptide in order to change its immunological properties. The attachment of the mPEG polymer to the peptide was at the carboxy terminus apparently leaving a free reactive amine functional group at the other terminus.

It is known, however, that heterogenous mixtures of "PEGylated" polypeptides and peptides are unsuited for pharmacological purposes (see e.g., PCT International Application, Pub. No. 90/12874). Indiscriminately conjugated proteins and peptides almost invariably will be expected to contain a mixture of molecular species or derivatives.

The use of tolerogenic antigens, alloantigens and allergens has received recent interest from the medical community for the treatment of auto-immune type disease. As noted above, typically the methods of the prior art utilize randomly derivatized whole antigen. Certain models of these diseases are known, however, which may serve as a testing ground for new approaches.

Where mixtures of indiscriminately derivatized peptides such as the specific epitopes described above are used as tolerogens, problems associated with reproducibility and efficacy are common. In particular, in cases where autoimmune disease are the result of limited specific epitopes being the target of the autoimmune antibodies, tolerogenic mixtures are not desirable. What are needed are specifically-derivatized, epitope-specific conjugated peptides. More particularly, methods of detecting autoantibodies in the sera of affected patients which do not yield very low or false negatives are needed. Moreover, integrated approaches to detection and treatment are needed for autoimmune diseases such as myasthenia gravis.

SUMMARY OF THE INVENTION

The present invention overcomes at least some of the problems existing in prior art approaches to the construction of reagents for the detection and treatment of autoimmune diseases such as myasthenia gravis by providing, for the first time, an integrated approach to diagnosing and treating the disease. In one aspect, the invention provides compositions and methods which allow the accurate and sensitive detection of autoantibodies in sera of patients suspected (by symptomatology) of having myasthenia gravis. In another aspect, the invention provides a synthetic method for construction of specifically-modified peptides covalently attached to a polymer which renders the synthetic peptide tolerogenic. In another aspect, the invention provides the use of these specifically-modified synthetic peptides in the treatment of diseases of autoimmunity and other unwanted responses such as allergic reactions and graft rejections. In yet another aspect, the invention provides for the reagents designed to immunosuppress undesirable immune responses. The invention also provides a method of testing such reagents for efficacy as immunosuppressants.

Thus, in a first embodiment, a method is disclosed of detecting autoantibodies associated with an immune disease. Generally, autoantibodies are those antibodies produced by a patient's own immune system in response to the patient's own antigen. Typically, such antigens will be associated with protein or peptide which is a natural constituent of the patient's own body.

The method comprises obtaining a peptide which corresponds to an epitope which is suspected of inducing an immune response of immune diseases such as myasthenia gravis. The immune disease myasthenia gravis is a disease where the patient's own immune system attacks the patient's own neurological system. In myasthenia gravis, particular proteins and peptides have been shown by the inventors to represent the points of attack. These points of attack are known as epitopes and are typically associated with the acetylcholine receptor of the human nerve ending. Thus, in one embodiment, it is the detection of the autoantibodies directed toward the patients own acetylcholine receptor antigen, and particularly toward the epitopes associated with that receptor, that is made possible with the methods of the invention.

A peptide so constructed may be used in testing of a serum sample of a patient suspected of having, or likely to develop, myasthenia gravis. While peripheral blood sera is preferred, other sources of the patient's sera will also serve so long as the serum is one which is known to contain the circulating autoantibodies associated with the immune disease.

A patient who may benefit from such testing will be any patient exhibiting the symptoms of myasthenia gravis such as lack of muscle tone, drooping eyelids, general musculatory weakness, and other well known symptoms. Patients who are suspected of having, have or who are at risk to develop such a disease include those with known family histories or who have entered into a non-symptomatic condition and who wish to be monitored for relapses.

After the peptide is contacted with the patient's serum, the degree of binding of any autoantibodies present in the serum to the peptide is determined. The degree of binding is determined by any of a number of techniques known well to those of skill in the art and which preferred techniques are disclosed herein. Thus, in one preferred embodiment, the peptide used to detect binding of autoantibodies will be one which has been labelled with a radioactive label such as an isotope of iodine.

The methods of the invention may also comprise producing a cocktail of at least two peptides for use in the detection method. The peptides are selected in a similar fashion to that described above for a single peptide and mixed to produce the cocktail. Of course, such a cocktail may comprise a pair of peptides so selected or it may equally well comprise combinations of more than two such peptides. In preferred embodiments of the present invention, cocktails of peptides with greater than two peptides are disclosed.

Each of the peptides utilized to construct a diagnostic cocktail will preferably be peptides corresponding to a distinct and different epitope which is suspected of inducing an immune response of myasthenia gravis. Similarly to the method using only a single peptide, the cocktail is used in contacting a serum sample of a patient suspected of having, or likely to develop, the disease and, determining the degree of binding of the autoantibodies to the cocktail.

The methods of the invention are preferably practiced using peptides selected from the group of peptides comprising the peptides in Sequence ID Nos. 7–25. Where a cocktail of peptides is used comprising at least two peptides, these peptides will be preferably selected from the group of peptides in Sequence ID Nos. 7–25. Thus, a reagent for use in a diagnostic assay is produced comprising either a peptide selected from the group of peptides in Sequence ID. Nos. 7–25 or, more preferably, a reagent is produced comprising a peptide selected from the group of peptides in Sequence ID Nos. 8, 17, 18 or 23. Similarly, where a cocktail of peptides is used in the diagnostic assay, the cocktail will comprise at least two peptides selected from the group of peptides in Sequence ID Nos. 7–25 or, more preferably, the cocktail of peptides will comprise at least two peptides selected from the group of peptides in sequence ID Nos. 8, 17, 18 or 23.

The methods of the invention will preferably be applied using a diagnostic kit comprising a single peptide reagent or a multiple peptide cocktail and an immunodetection reagent. Such a kit will contain those tools necessary for application of the methods as taught in the present disclosure such as test tubes, assay tubes, and the other necessary articles disclosed in the present invention. As pointed out previously, the detection of the binding of the autoantibodies to the reagent or cocktail may be carried out in a number of ways known well to those of skill in the art, but most preferably due to its sensitivity, a radioactive immunodetection reagent will be used.

In a second embodiment, the invention provides methods for peptide synthesis and, in particular, synthesis tolerogenic polymer-derivatized peptides or groups of peptides useful in treating an immune disease such as myasthenia gravis. The method for producing such reagents entails producing a peptide covalently linked via its carboxy-terminal amino acid to a synthetic resin. It will be understood well by those of skill in the art that due to its ease, coupling of the carboxy terminus to the synthetic resin is only one manner in which to provide a single free, amino terminus for subsequent derivatization. However, the same skilled artisan will also realize that it is possible to use alternative protocols to specifically block the amino terminus and to derivatize the carboxy terminus of such a peptide. Therefore, while the preferred technique will involve a carboxy terminus attached to a synthetic resin and a free amino terminus, derivatization of either or both termini is anticipated by the present inventors to give equally efficient tolerogenic peptides.

Any of the synthetic resins known to those of skill in the art will be amenable to the methodology of the invention. For instance, one may use synthetic methods based on either t-butyloxycarbonyl (t-Boc) derivatized amino acids synthesized on a phenylacetamidomethyl (PAM) resin or by 9-fluorenmethylcarbonyl (Fmoc) derivatized amino acids on a benzyloxybenzyl alcohol resin (McCormick and Atassi 1984; Mulac-Jericevic and Atassi, 1987; Atassi et al., 1991).

The peptides of the invention will typically be protected from inadvertent coupling along the side chains by the presence of side chain-protected amino acids in the peptide. It will be well understood by those of skill in the art that such side chain protecting groups can vary depending upon the nature of the synthetic procedure.

In the preferred embodiment, the peptide may be synthesized beginning with any sized initial peptide fragment attached by its carboxy terminus to the resin. Thus, it will be understood by those of skill in the art that one may obtain presynthesized and derivatized peptides of variable lengths. Alternatively, one may obtain from any number of commercial sources synthetic resins which have one or more derivatized amino acids coupled to the resin by its carboxy terminus. The invention, therefore, is not limited to the use of wholly synthetic peptides and may include peptide fragments derived from native antigens themselves or from antigens obtained using recombinant DNA technology so long as these peptides may be protected along their side chains and covalently bound to a resin at their carboxy or amino terminus.

The peptides produced by the methods of the invention will typically correspond to an epitope which is suspected of inducing an autoimmune response or other undesired responses such as allergic conditions or graft rejections. Such an epitope may be suspected for any number of reasons. There may be empirical data which indicate a specific and relatively restricted epitope as a linear sequence found as an identical sequence in the native antigen known to cause the immune response of the disease. Alternatively, such an epitope may be a non-linear sequence corresponding to an antigenic region of a native antigen but which linear sequence does not exist as such in the native antigen.

Moreover, the peptides produced by the invention may be potential epitopes due to localization to a region known to contain the minimally-sized epitope inducing the maximal antigenic response in the immune disease. For instance, it is known by those of skill in the art that many cell membrane-associated antigens chiefly present the extracellular portions of the polypeptide as potential epitopes. Thus, the epitope suspected of inducing the immune response may only be suspected as a battery of potential epitopes which are typically presented in the physiological state. In some cases, therefore, one may wish to test a battery of overlapping peptides representing sequential segments of the exposed extracellular regions of a given native antigen.

The peptide so selected and/or synthesized is attached to a resin by one of its termini, preferably by its carboxy-terminus, and is then derivatized at its other, preferably amino, terminal amino acid with a tolerogenic polymer. Since all side chains which need protection will still be protected as they were during the synthetic procedure, and since one terminus is likewise protected by coupling to the resin, the only reactive group will occur at the other terminus, preferably at the growing N-terminal amino acid as the $\alpha$-$NH_2$ of that terminal residue. It is to this terminus that the tolerogenic polymer is attached.

The methods of the invention complete the synthesis of the terminally protected, tolerogenic peptides by deprotecting the side chain-protected amino acids comprising the peptide. Depending on the nature of the synthetic chemistry used to construct the peptide, deprotection will be achieved variously by methods known well to those of skill in the art. Similarly, depending upon the resin used to initiate synthesis, cleaving the peptide from the resin will take various forms. Purification of the peptide will also take various forms depending upon the nature of the resulting peptide. In some cases, more hydrophilic peptides may be amenable to purification schemes depending upon the solubility of the peptide in water-based solvents. More hydrophobic peptides may require organic solvents and purification schemes in which the peptides will be most soluble.

Even though methods of the invention relate to any epitope-specific tolerogenic peptide used to construct reagents capable of treating immune diseases, the invention relates more specifically to certain characterized peptide reagents. Thus, the invention discloses the specific construction of any of the peptides shown in Sequence ID Nos. 1–25. Certain of these specific peptide reagents relate to specific immune diseases such as myasthenia gravis, ragweed pollen allergy, and Grave's disease. Moreover, the methods of the invention relate to specific native polypeptides such as a subunit of an acetylcholine receptor, ragweed pollen antigen Ra3, or a polypeptide subunit of the thyroid-stimulating hormone receptor responsible for Grave's disease.

It is preferred that the peptide reagent designed will be directly or indirectly responsible for the major immune response as the principal causative agent of symptoms of the immune disease. However, there may be instances where peptides corresponding to regions of the native antigen responsible for lesser immune responses will be desired. In particular, combinations of reagents, each of which accounts in part for the immune response, may be preferred in certain instances.

The methods of the invention employ the covalent coupling of a tolerogenic polymer to the peptide reagents. Such tolerogenic polymers are known well to those of skill in the art. For instance, such a polymer may be polyethylene glycol or a polyethylene glycol derivative. In a preferred embodiment of the invention, the monomethoxy derivative of polyethylene glycol will be used. Alternatively, polyvinyl alcohol or a derivative of polyvinyl alcohol may be used. Still other such polymers are known including polysaccharides such as dextrans.

In any instance, the basic polymer selected will be treated in a manner as to make the polymer amenable to a coupling reaction. In a preferred embodiment, the method used to derivatize the polymer will involve succinylation of the polymer so as to derivatize the hydroxyl groups of the polymer and to generate any number of reactive carboxyl groups. Complete derivatization is monitored as is availability of the reactive carboxy groups on the surface of the modified polymer.

In another principal aspect of the invention, a method of treating an autoimmune disease is disclosed. The method consists of first administering a tolerogenic polymer-derivatized peptide. The peptide reagent so administered will typically correspond to an epitope which is suspected of inducing an autoimmune response of the disease. The patient to whom the peptide is administered may be one who has or is suspected of having the disease. Alternatively, the patient may be one who is likely to develop the autoimmune disease.

For instance, certain autoimmune diseases have long non-symptomatic episodes in which major immune responses are not present. In the autoimmune disease myasthenia gravis, patients typically experience sometimes very lengthy non-symptomatic periods followed by periods of almost complete debilitation due to the ongoing immune response. The patient is thus treated at an optimal time with tolerogenic peptide, preferably prior to onset of a major autoimmune response to the natural antigen from which the epitope was designed.

Reagents useful in the treatment of an autoimmune disease are also disclosed in the present invention. Generally, such a reagent will be a peptide corresponding to an epitope which is suspected of inducing an autoimmune response which peptide is derivatized at an N-terminal amino acid of the peptide with a tolerogenic polymer.

More specifically, the reagent will be one of the group of peptides disclosed in Sequence ID Nos. 1–25. It will be recognized, however, by those of skill in the art that the reagent peptides may contain functionally equivalent amino acid substitutions. The importance of the hydropathic index of amino acids in conferring biological function on a protein has been discussed generally by Kyte and Doolittle (1982). It has been found by these researchers and others that certain amino acids may be substituted for other amino acids having a similar hydropathic index or score and still retain similar if not identical biological activity. As displayed in Table I below, amino acids are assigned a hydropathic index on the basis of their hydrophobicity and charge characteristics. It is believed that the relative hydropathic character of the amino acid determines the secondary structure of the resultant protein, which in turn defines the interaction of the protein with the substrate molecule. Similarly, in peptides whose secondary structure is not a principal aspect of the interaction of the peptide, position within the peptide and the characteristic of the amino acid residue determine the interactions the peptide has in a biological system. It is proposed that biological functional equivalence may typically be maintained where amino acids having no more than a ±1 to 2 difference in the index value, and more preferably within a ±1 difference, are exchanged.

TABLE I

| AMINO ACID | HYDROPATHIC INDEX |
|---|---|
| Isoleucine | 4.5 |
| Valine | 4.2 |
| Leucine | 3.8 |
| Phenylalanine | 2.8 |
| Cysteine/Cystine | 2.5 |
| Methionine | 1.9 |
| Alanine | 1.8 |
| Glycine | -0.4 |
| Threonine | -0.7 |

TABLE I-continued

| AMINO ACID | HYDROPATHIC INDEX |
|---|---|
| Tryptophan | -0.9 |
| Serine | -0.8 |
| Tyrosine | -1.3 |
| Proline | -1.6 |
| Histidine | -3.2 |
| Glutamic Acid | -3.5 |
| Glutamine | -3.5 |
| Aspartic Acid | -3.5 |
| Asparagine | -3.5 |
| Lysine | -3.9 |
| Arginine | -4.5 |

Thus, for example, isoleucine, which has a hydropathic index of +4.5, can be substituted for valine (+4.2) or leucine (+3.8), and still obtain a protein having similar biologic activity. Alternatively, at the other end of the scale, lysine (−3.9) can be substituted for arginine (−4.5), and so on.

Accordingly, these amino acid substitutions are generally based on the relative similarity of R-group substituents, for example, in terms of size, electrophilic character, charge, and the like. In general, although these are not the only such substitutions, the preferred substitutions which take various of the foregoing characteristics into consideration include the following:

TABLE II

| Original Residue | Exemplary Substitutions |
|---|---|
| Ala | gly; ser |
| Arg | lys |
| Asn | gln; his |
| Asp | glu |
| Cys | ser |
| Gln | asn |
| Glu | asp |
| Gly | ala |
| His | asn; gln |
| Ile | leu; val |
| Leu | ile; val |
| Lys | arg; gln; glu |
| Met | met; leu; tyr |
| Ser | thr |
| Thr | ser |
| Trp | tyr |
| Tyr | trp; phe |
| Val | ile; leu |

More particularly, the invention relates to a method of producing reagents useful in the treatment of myasthenia gravis. In such a method, a peptide is synthesized corresponding to the peptide shown in Sequence ID No. 5. This peptide is covalently linked during and after synthesis to a carboxy-terminal amino acid of the peptide to a resin and possesses side chain-protected amino acids. As is described in more detail below, this peptide corresponds to an epitope which is suspected of inducing a myasthenia gravis autoimmune response. The peptide is then derivatized at an N-terminal amino acid of said peptide with mPEG. Following derivatization with the tolerogenic polymer, the reagent is deprotected along its the side chain-protected amino acids, cleaved from the resin, and purified. Even though such a specific reagent is disclosed, it will be understood that other myasthenogenic peptides will be amenable to the general methods of the invention in order to produce suitable reagents for treatment of the disease alone or in combination with other drugs and treatments.

A similar method is disclosed relating to production of reagents useful in the treatment of ragweed allergy. In the case of the specific ragweed peptide disclosed herein, the peptide will correspond to the peptides shown in Sequence ID Nos. 1–4. Similarly, a method of producing reagents useful in the treatment of Grave's disease are disclosed herein. Reagents produced by any of the methods of the invention as they relate to Grave's disease are also disclosed (See, Atassi et al. *Proc. Ntl. Acad. Sci USA* 88:3613–3617 [1991], specifically incorporated by reference herein).

Methods of treating myasthenia gravis, ragweed allergy, and Grave's disease are disclosed in specific embodiments. In certain preferred embodiments, these methods will more particularly utilize an mPEG-derivatized peptide corresponding to those peptides identified in Sequence ID Nos. 1–25.

In another major aspect of the invention, methods of screening reagents potentially useful in the treatment of autoimmune diseases are disclosed. In a general application of this method, one produces a peptide covalently linked via one of its terminal ends, such as the N-terminal amino acid, of the peptide to a resin such as those disclosed below, protecting the amino acid residues accordingly with side chain-protecting groups. The candidate peptide will typically correspond to an epitope or an amino acid sequence from a region believed to contain such an epitope, which is suspected of inducing an autoimmune response. The candidate reagent will be completed by derivatizing the N-terminal $\alpha$-NH$_2$ (or the C-terminal carboxyl) of the peptide with a tolerogenic polymer, deprotecting the side chain-protected amino acids comprising the peptide, cleaving the peptide from the resin, and purifying the peptide.

As a next step in the screening method, a test subject having, or likely to develop, the immune (such as an autoimmune) disease or an experimental model of the immune disease is treated with the peptide reagent. The treatment will preferably occur prior to onset of an immune response to an autoantigen (or allergen) or transplantation antigen) comprising the epitope. Finally, the test subject will be evaluated for alleviation of symptoms related to said immune response.

It will be understood by those of skill in the art that the method of screening generally outlined above will typically be applied where the peptide under investigation is one of a battery of peptides whose sequences are derived in some manner from the native protein suspected of causing the immune response. Methods of treatment of the test subject may vary according to the nature of the reagent or the strictures of the testing protocols, but typically will involve the injection of the peptide reagent into the test subject at selected intervals and without an adjuvant.

A method of screening reagents potentially useful in the treatment of myasthenia gravis, is described, for instance, which involves producing peptides using the methods described herein based upon the extracellularly accessible regions of certain polypeptide subunits of the acetylcholine receptor. The test subject is then treated with the tolerogen-peptide conjugate. The test subject may be a human test subject having, or likely to develop, myasthenia gravis. Alternatively, and in a preferred embodiment where experimental drugs are first screened, the test subject may be a non-human animal such as a mouse in which experimental autoimmune myasthenia gravis has been induced using injections of the native antigen, acetylcholine receptor derived from Torpedo. As described previously, one wishing to use such a screening method will typically administer the peptide reagent to the test subject prior to onset of an autoimmune response to an acetylcholine receptor polypeptide. Following treatment, the test subject will be evaluated for alleviation of symptoms related to myasthenia gravis or an experimentally induced model thereof. Where possible, evaluation of the test subject for alleviation of symptoms further comprises evaluating the test subject using electrophysiological criteria.

BRIEF DESCRIPTION OF THE DRAWINGS

FIG. 1. Covalent structure of certain synthetic peptides used in the present work for coupling to mPEG and to PVA. Peptide 1 was synthesized on a PAM-resin by t-Boc amino acids as described earlier (from McCormick and Atassi, 1984). Peptides 2–6 were synthesized on a benzyloxybenzyl alcohol resin by Fmoc amino acids.

FIG. 2. Scheme for synthesis of mPEG-peptide and PVA-peptide conjugates. In step A, the aliphatic hydroxyl groups on mPEG and PVA are reacted with succinic anhydride. In step B, the synthetic peptide, while still on the resin with all the side-chain protecting groups intact, is deprotected at the $\alpha$-NH$_2$ group only (compound 2) and then coupled through this now free amino group to the carboxyl group of compound 1 using a carbodiimide and an excess of compound 1. Complete blocking of the amino group is monitored and recoupling is performed if necessary. When free amino groups are no longer detectable, the peptide is cleaved from the resin. This scheme is a general procedure for the synthesis of mPEG-peptide and PVA-peptide conjugates (compound 3). The peptide conjugate is then lyophilized and subjected to purification.

peptide α125-148; (B), whole AChR; (C) peptide α45-60 and (D) peptide α182-198 as described in the text. In A, Group 1 mice showed significant suppression of the antibody population that binds with peptide α125-148 (mean net cpm ± standard deviation=1414±1801 compared to the mice in Group 2 (3334±2318, p<0.005) and Group 3 (3626+2214, p<0.005). Antibodies against whole receptor (shown in B; P>0.5), peptide α45-60 (shown in C; P>0.1–0.5) and peptide α182-198 (shown in D; P>0.1–0.5) suffered no significant suppression in Group 1 compared to the control groups.

Figure 9:
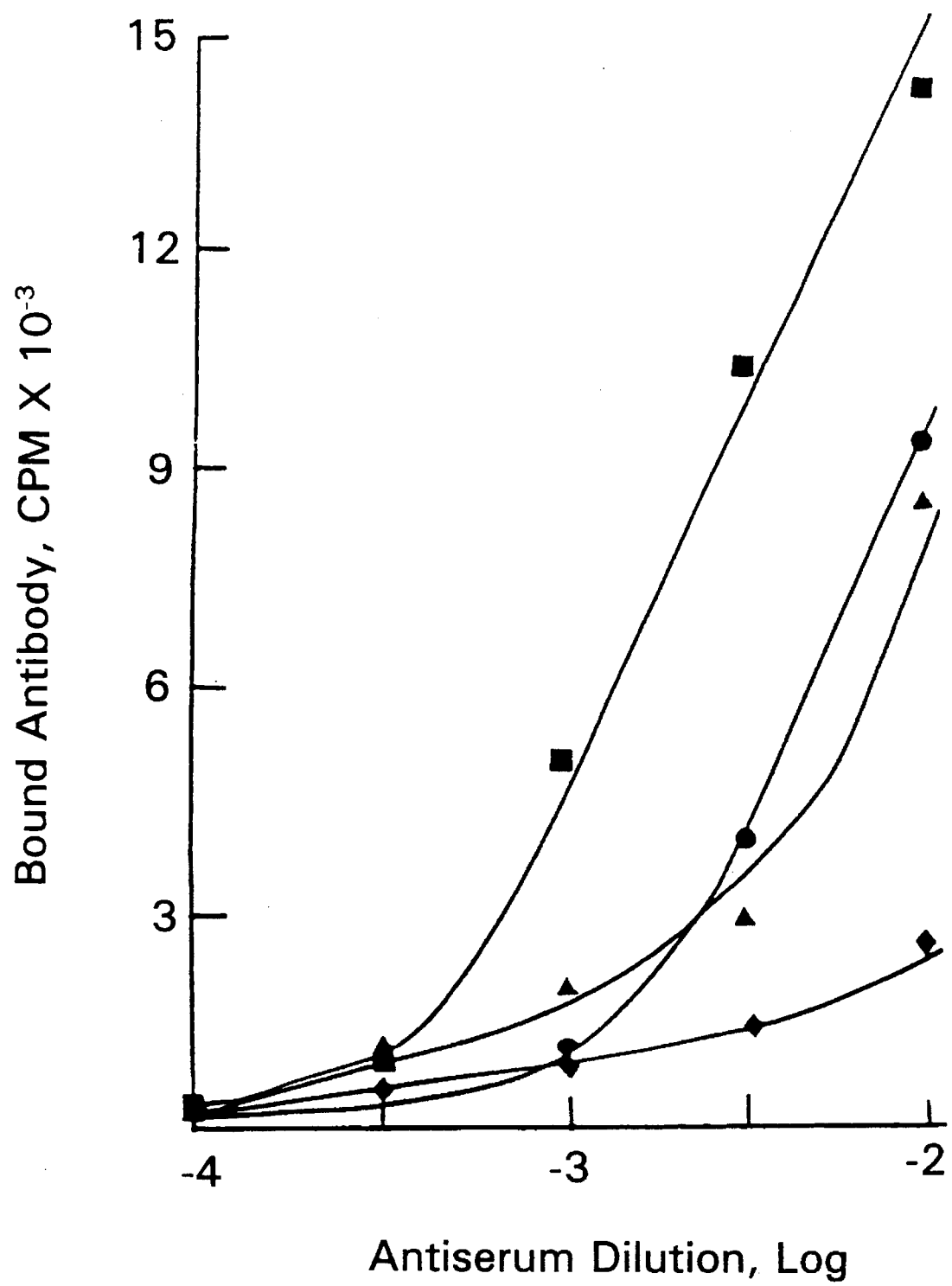

FIG. 9. Binding to peptide α125-148 of anti-AChR antibodies in pooled antisera from each group of mice (see FIG. 6). Antisera were studied at various dilutions as shown. The pooled antisera from Group 1 mice (♦) showed considerably lower antibody binding to the peptide than antibodies from Groups 2 (●), 3 (■), and 5 (△) (see text).

Figure 10A:
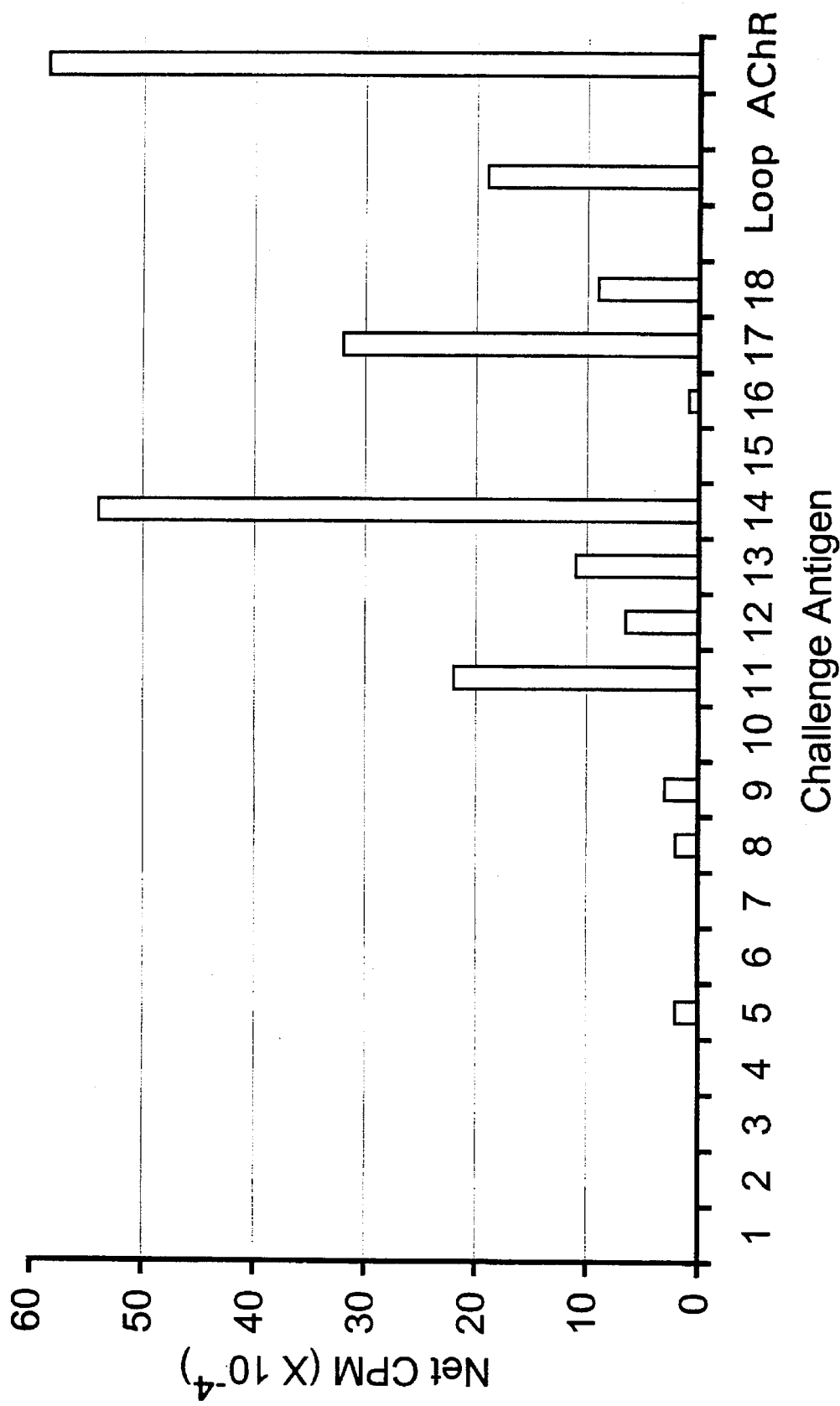
Figure 10B:
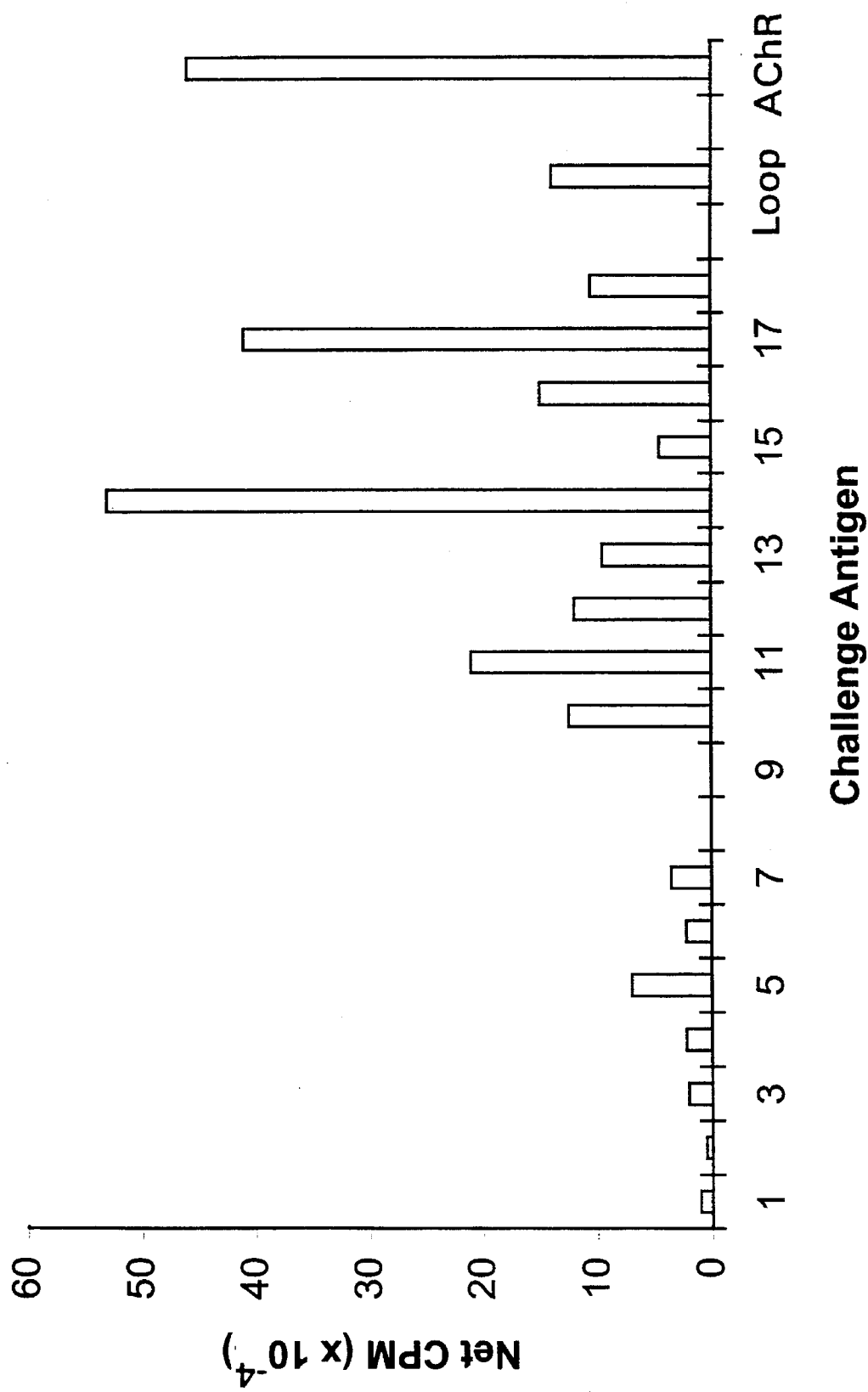

FIG. 10. Effects of pre-administration of mPEG-(α125-148) on the T cell proliferative responses after immunization with AChR. The T-cell recognition profiles (B) of EAMG-negative mice (C57/BL6) from Group 1 and EAMG-positive mice (A) from Group 2 were mapped with uniform sized, overlapping synthetic peptides corresponding to the entire extracellular part of the α chain of Torpedo AChR (Mulac-Jericevic et al., 1987a,b) and with peptide α125-148 (loop) (McCormick and Atassi, 1984). In these assays LNC ($5 \times 10^5$ cells/well) were challenged in vitro with various doses of peptide (10–40 μg/ml), AChR (1.5–6.0 ug/ml). Nonsense peptide, lysozyme and ovalbumin were used as negative controls and added to the cells in the same dose ranges for peptides and AChR, respectively. Concanavalin A (1 μg/ml) was used as a positive control. The results were done in triplicate and repeated twice. EAMG-positive and EAMG-negative mice were selected on the basis of the EMG test.

FIG. 11. Structure of the synthetic overlapping peptides representing the main extracellular part (residues α1-210) (Mulac-Jericevic et al. 1988) and a small extracellular region (residues α262-276) (Atassi et al. 1988) between two transmembrane regions, of the α-chain of the human AChR. The regions of overlaps between consecutive peptides are bolded. The single letter notations of the amino acids are: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; Y, Tyr.

Figure 12:
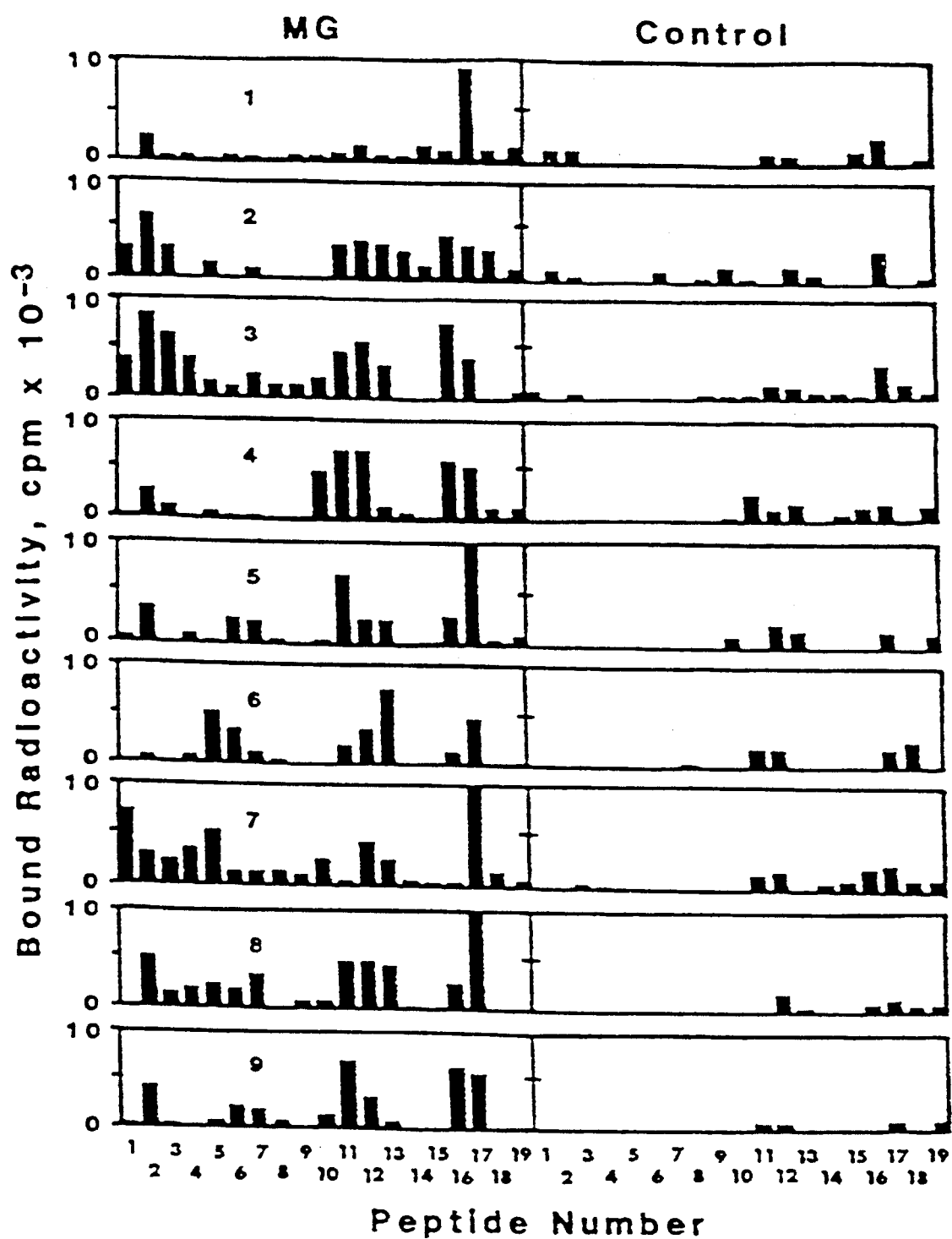

FIG. 12. Summary of the binding profiles of the autoantibodies in MG plasma and normal human plasma to the synthetic peptides (FIG. 11). The binding assays were performed as described in the text.

Figure 13:
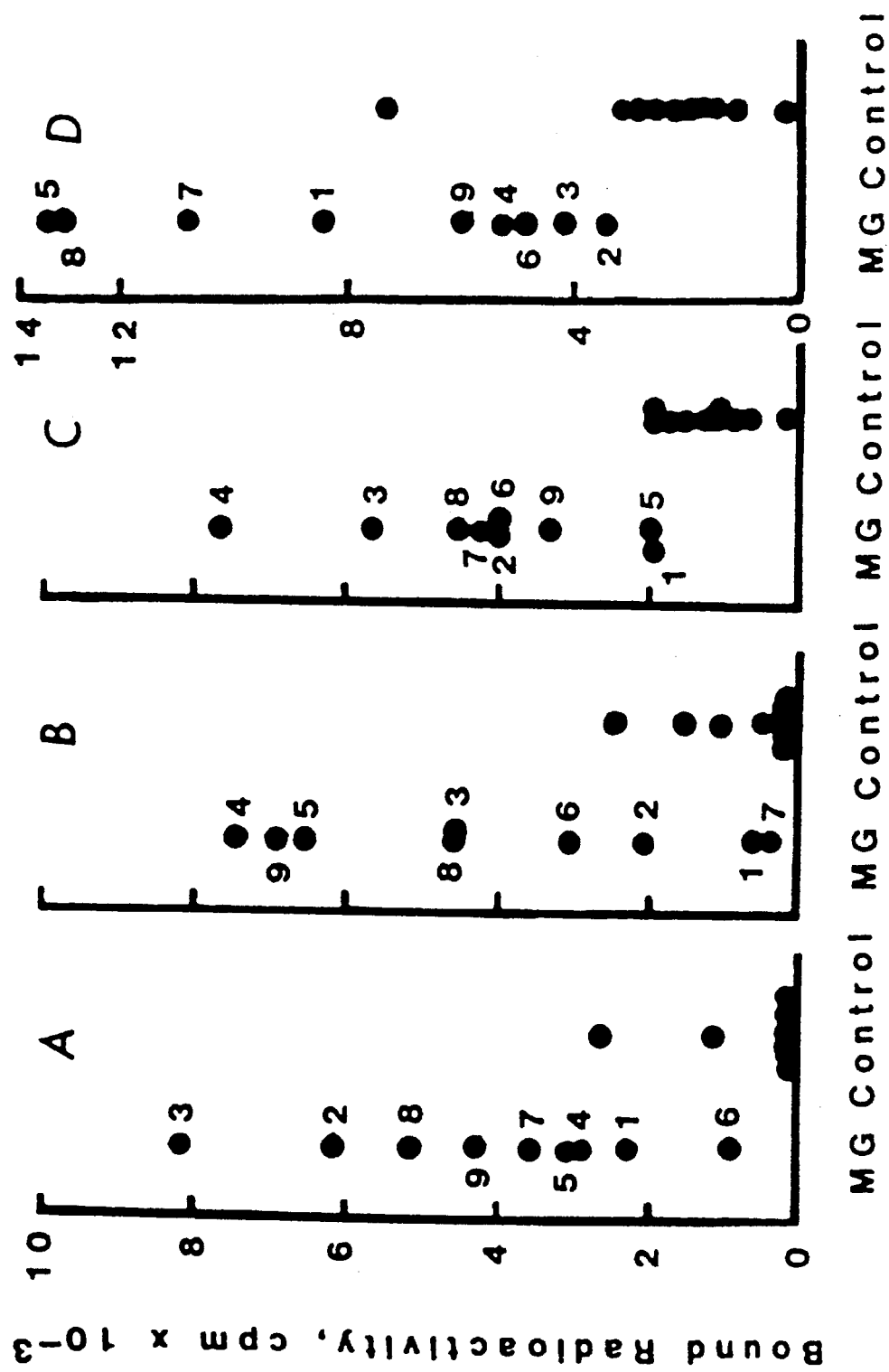

FIG. 13. Binding of autoantibodies in nine MG plasma samples and in control human plasma from nine normal individuals to each of the peptides α12-27(A), α111-126(B), α122-138(C) and α182-198(D). The binding activity in MG samples was considered significant when it was at least two times higher than the normal plasma samples.

Figure 14:
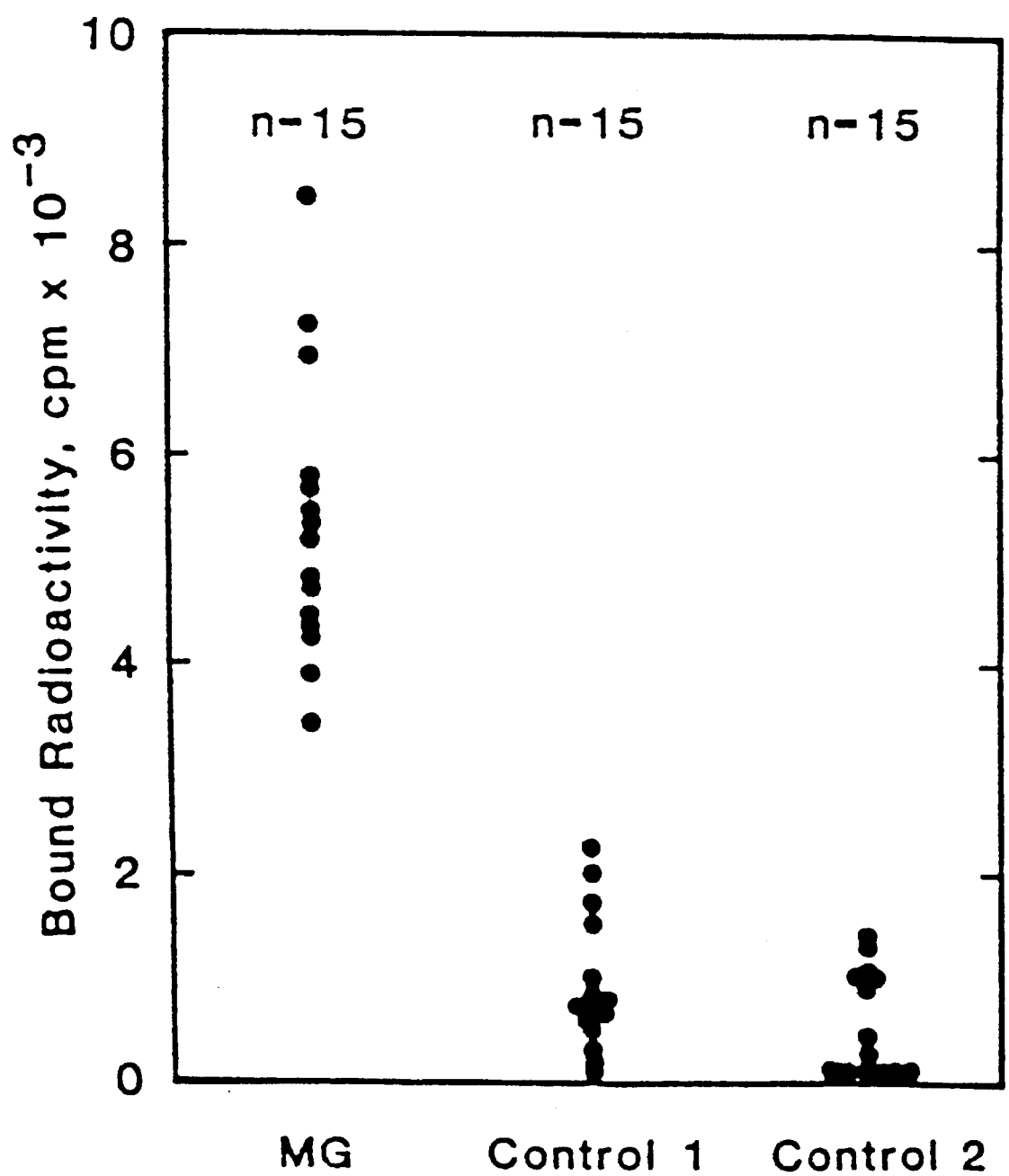

FIG. 14. Binding of antibodies in plasma samples from fifteen MG patients, fifteen individuals suffering from other neurological or autoimmune diseases (Control 1) and fifteen normal individuals (Control 2) to a mixture of peptides α12-27, α111-126, α122-138 and α182-198. The plasma samples were diluted (1:200, v/v) with PBS containing 0.2% casein. The MG plasma samples showed significant binding (mean net cpm 5,278±1,398, p<0.001) compared to the other diseases (Control 1, mean net cpm 956±652) and the normal plasma samples (Control 2, mean net cpm 518±564).

Figure 15:
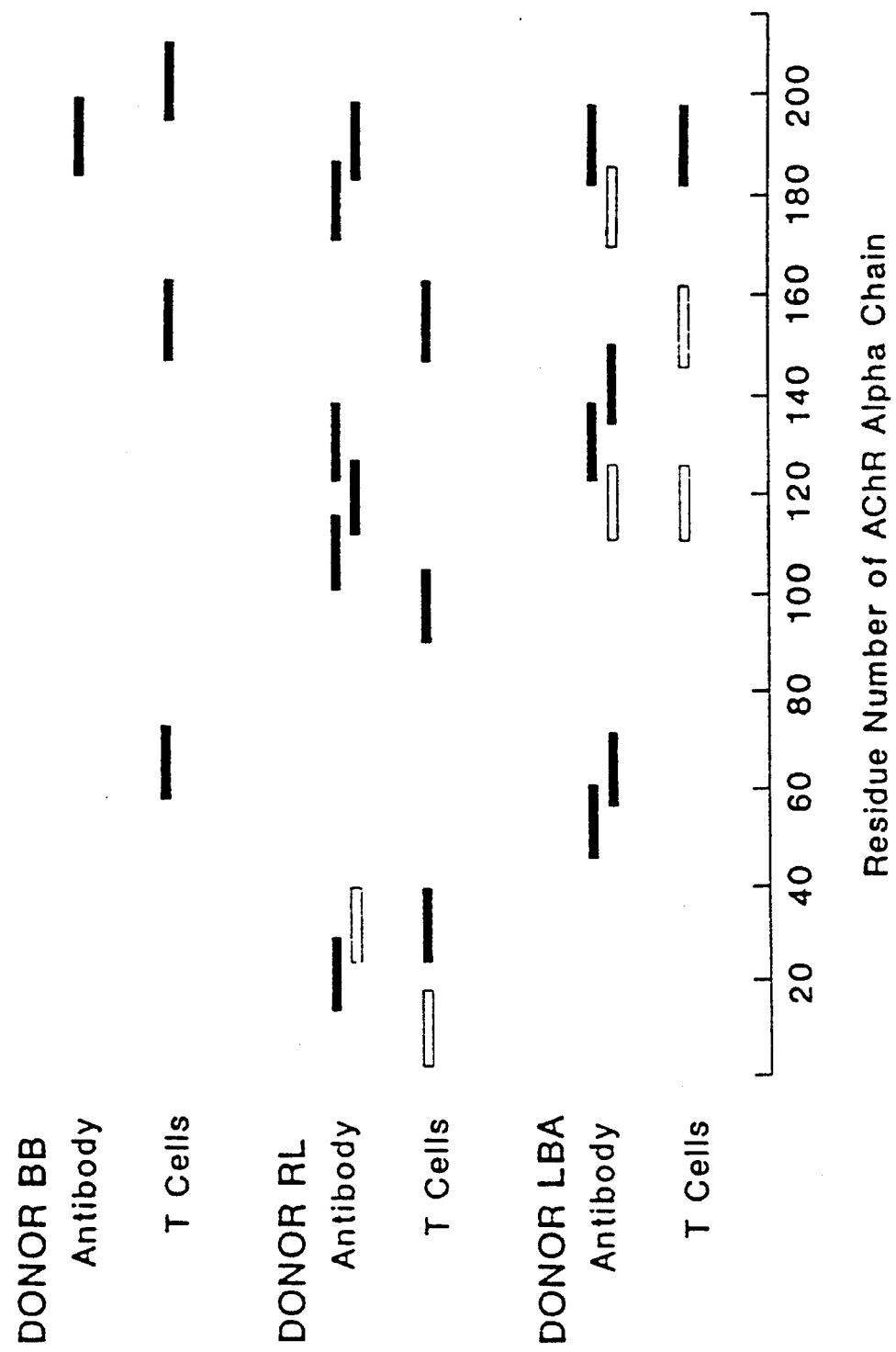

FIG. 15. Comparison of autoimmune antibody and T-cell peptide recognition profiles of the extracellular part of human AChR α-chain in two MG patients. The results of peptide recognition by autoantibodies were obtained in the present work. The T-cell recognition profiles for T-cell lines originating from the same two peptides were obtained from Oshima et al (Oshima et al. 1990). The bars indicate the locations of the stimulating peptides in the sequence. Solid bars represent a strong response while open bars denote an intermediate response. The patient numbers MG4 and MG6 in this figure correspond, in reference (Lindstrom et al. 1976), to patient numbers MG9 and MG7, respectively.

DESCRIPTION OF PREFERRED EMBODIMENTS

In general aspects, certain protocols and procedures will be applicable to the various methods and compositions of matter of the invention. These general techniques are detailed below.

Peptide Synthesis and Purification

The peptides used for certain particular examples of the invention are shown in FIG. 1 and correspond to the Sequence ID Nos. 1–6. These peptides, as well as other peptides produced using the methods of the invention, were synthesized either by t-butyloxycarbonyl (t-Boc) on a phenylacetamidomethyl (PAM) resin or by 9-fluorenmethylcarbonyl (Fmoc) amino acids on a benzyloxybenzyl alcohol resin as described elsewhere (McCormick and Atassi 1984; Mulac-Jericevic and Atassi, 1987; Atassi et al., 1991), together with methods for purification and characterization of the peptides. Other synthetic procedures can be utilized as well so long as the synthesis results in biologically active peptides.

Succinylation of the Hydroxyl Groups of mPEG and PVA

To prepare the succinate esters of mPEG and PVA, one gram of mPEG (molecular weight, 5000) or PVA (molecular weight 3,000) is dissolved in 5 ml anhydrous pyridine at 50° C., and to these solutions aliquots of succinic anhydride (0.5 g each) are added as a dry powder at 1-hour intervals. Following the last addition, the reaction mixture is stirred for 2 hours at 50° C., after which it is evaporated to dryness on the flash evaporator. The residue is dissolved in water and evaporated to dryness and this washing with water on the evaporator is repeated several times until the odor of pyridine in the residue is very faint. The residue is dissolved in water (10 ml) and dialyzed, in a 1000-molecular weight cut-off dialysis membrane, against several changes of distilled water and finally freeze-dried (yield 0.92–0.95 g). Complete succinylation of the polymers is confirmed by a negative reaction for hydroxyl and a positive reaction for carboxyl groups.

Determination of Hydroxyl and Carboxyl Groups in the Polymers

Determination of hydroxyl groups is carried as follows. A solution of test sample (365 μl containing 2 mg of mPEG, PVA mPEG-Su, PVA-SU, succinic anhydride, and standards containing various amounts of methanol from 0 to 1.5 μmole in 0.06M sodium phosphate buffer pH 7.5, containing 0.09M NaCl, is mixed with 182 μl of 0.75M perchloric acid. A blank is prepared which contains the same reagents but without a test sample. After mixing, the tubes are centrifuged (2000 rpm, 20 min.) and 365 μl aliquots from each tube are transferred to clean test tubes. To each tube is added 40 μl of 2% $KMnO_4$ (in water), the solutions are mixed for exactly 1 minute, then 40 μl of freshly prepared 10% sodium sulfite (in water) is added and the tubes are immediately shaken vigorously. At this point, the solutions should become completely decolorized. To these solutions is added 1.45 ml of chromotropic acid reagent [8 mg of 4,5-dihydroxy-2,7-naphthalene-disulfonic acid disodium salt (Sigma Chemical Co., St. Louis, Mo.) dissolved in 0.10 ml $H_2O$ and 1.35 ml sulfuric acid solution (Conc. $H_2SO_4$/water, 2:1, v/v)]. The tubes are covered and placed in boiling water for 15 min. after which they are cooled to room temperature and the absorbance of the solutions is read at 580 nm against the blank solutions in the reference cell. The hydroxyl group content of a sample is determined based on the methanol standard curve of absorbance versus amount of methanol ($A^{1cm}_{580}$ for 1 µmole of $CH_3OH$=0.856).

Carboxyl groups are detected by the following method. An aliquot of a water solution of the test sample (20 µl containing 1 mg of mPEG, PVA mPEG-Su or PVA-SU) is applied as a spot on Whatman No. 3MM Chr paper. The spot is dried with cold air and the paper is then stained by spraying with a solution of 0.04% bromothymol blue in ethanol, preadjusted to pH 8.0 with 0.2M boric acid. mPEG-Su and PVA-Su give bright yellow spots on a blue background, whereas the spots of mPEG and PVA appear blue.

Coupling of mPEG or PVA Succinates to Synthetic Peptides

A coupling method for the preparation of mPEG-peptide and PVA-peptide conjugates is illustrated in FIG. 2. The synthesis resin (0.1 g) carrying the completed synthetic peptide (0.025 m mole), with all the side chain protecting groups intact, is swollen in a synthesis vessel in methylene chloride overnight. The t-Boc protecting group on the α-amino group of the synthetic peptide is removed by treatment with 40% trifluoroacetic acid containing 2% anisole and 2% dimethylformamide (DMF) at room temperature for 30 minutes. For the Fmoc-peptides, the $N^α$-Fmoc protecting group is removed by 20% piperidine in DMF. For coupling of mPEG-Su, a three-molar excess in 1.5 ml of DMF is reacted with 0.2 ml of 50% dicyclohexylcarbodiimide (DCC) or diisopropylcarbodiinide (DIPC) in methylene chloride for 20 minutes, filtered to remove dicyclohexyl urea (if DCC is used), then added to the N-terminal-deprotected peptide-resin and allowed to react for 24 hours. For coupling of PVA-Su, larger reaction volumes are needed because of its tendency to gel. Three-molar excess of PVA-Su is dissolved in 8.0 ml of DMF and to this is added 0.20 ml of 50% DCC or DIPC in methylene chloride. Three cycles of recoupling of mPEG-Su or PVA-Su to the peptide-resin are done. The complete blocking of the α-$NH_2$ is confirmed by a ninhydrin test (Kaiser et al, 1970). After the α-amino group on the peptide is completely blocked, uncoupled mPEG-Su or PVA-Su is washed out of the vessel with methylene chloride and then methanol. The peptide conjugate is cleaved from the resin by HF (Sakakibara et al, 1967), if a PAM resin and t-Boc amino acids are used, or by treatment (2.5 hr) with 55% trifluoroacetic acid in methylene chloride if a benzyloxybenzyl alcohol resin and Fmoc amino acids are used.

Any residual uncoupled peptide is removed from the conjugate by gel filtration on a Sephadex G-75 fine column (1.5×75 cm) in 0.1M ammonium bicarbonate and by high pressure liquid chromatography (HPLC) on a size exclusion column (Waters protein pack 60, 0.7×30 cm) which is eluted with 0.2M ammonium bicarbonate containing 20% acetonitrile at a flow rate of 0.7 ml/min.

Preparation of Torpedo AChR

The purification of Torpedo AChR is carried out as described elsewhere (Froehner, 1979; Mulac-Jericevic and Atassi, 1987). Briefly, the electric organ of *Torpedo californica* (Pacific Bio-Marine Laboratories, CA) is homogenized and the membrane proteins are extracted in 1% Triton X-100 (Sigma Chemical Company, MO). After centrifugation, the AChR in the supernatant is affinity purified on a cobratoxin Sepharose CL4B column using 1M carbamylcholine in 1% octyl β-D-glucopyranoside (Sigma Chemical Company, MO) for the elution of the AChR. The purified AChR is composed of the expected four subunits (α, β, γ, δ) as demonstrated by SDS-PAGE (Laemmli, 1970).

Synthesis of Myasthenic Peptide ∝125-148 and Its mPEG Conjugates

The structure of peptide α125-148 (FIG. 1, Seq. ID No. 5) of Torpedo AChR was based on the amino acid sequence of the extracellular part of the receptor (Noda et al., 1982). The peptide was synthesized and purified as described by McCormick and Atassi (1984). Cyclization of the synthetic peptide α125-148 was performed under conditions previously described (McCormick and Atassi, 1984). The monomeric form was separated by gel filtration on Sephadex G-25 fine (Pharmacia Fine Chemicals) column in 0.1M ammonium bicarbonate. After purification, homogeneity of the monomeric peptide was confirmed by high-voltage paper electrophoresis (Atassi and Saplin 1968). The amino acid composition of the peptide was in excellent agreement with that expected from its sequence. A nonsense peptide, having a structure (HFKSFHSFSVSGETVFEVTEAG) totally unrelated to AChR, was also synthesized and employed as a negative control.

The coupling method for the preparation of mPEG-peptide conjugates is described above and in Atassi and Manshouri (1992).

Figure 4:
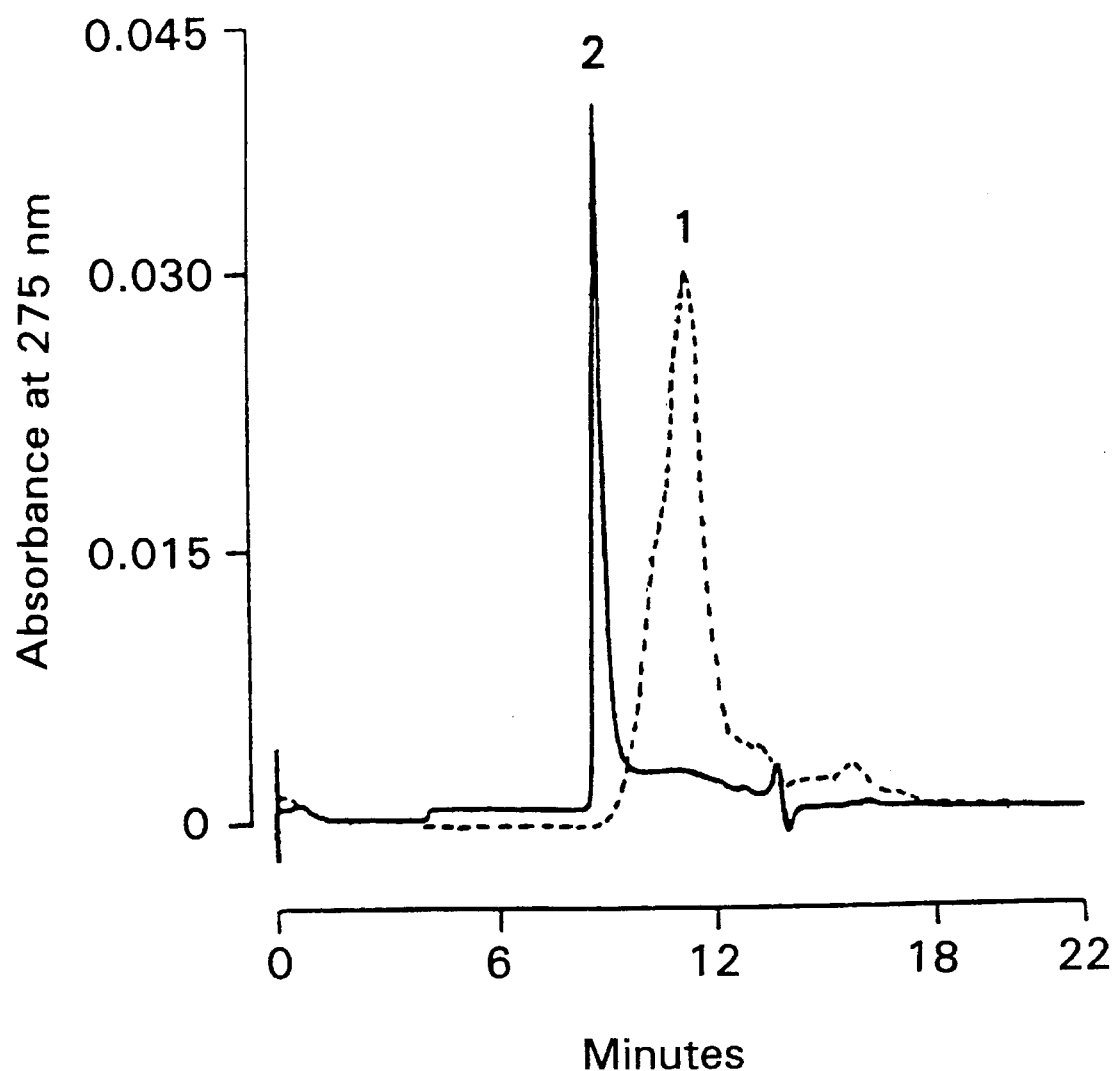
FIG. 4. Elution profiles of: (1) peptide $\alpha$125-148, and (2) mPEG-($\alpha$125-148) conjugate in HPLC on a size exclusion column (Waters protein pak 60, 0.7×30 cm). The column was eluted with 0.2M ammonium bicarbonate containing 20% acetonitrile at 0.70 ml/min.

After synthesis of the conjugates and cleavage from the synthesis resin, any residual uncoupled peptide was removed from the conjugate by gel filtration on a column (1.5×75 cm) of Sephadex G-75 fine in 0.1M ammonium bicarbonate. After lyophilization, the mPEG-(α125-148) conjugate was cyclized and the monomeric species isolated as described (McCormick and Atassi, 1984). A sample of the purified peptide-mPEG conjugate was confirmed to be free of the uncoupled peptide by high performance liquid chromatography (HPLC) on a size exclusion column (Waters protein pack 60, 0.7×30 cm) which was eluted with 0.2M ammonium bicarbonate containing 20% acetonitrile at a flow rate of 0.7 ml/min (FIG. 4).

Tolerization and Immunization

Figure 5:
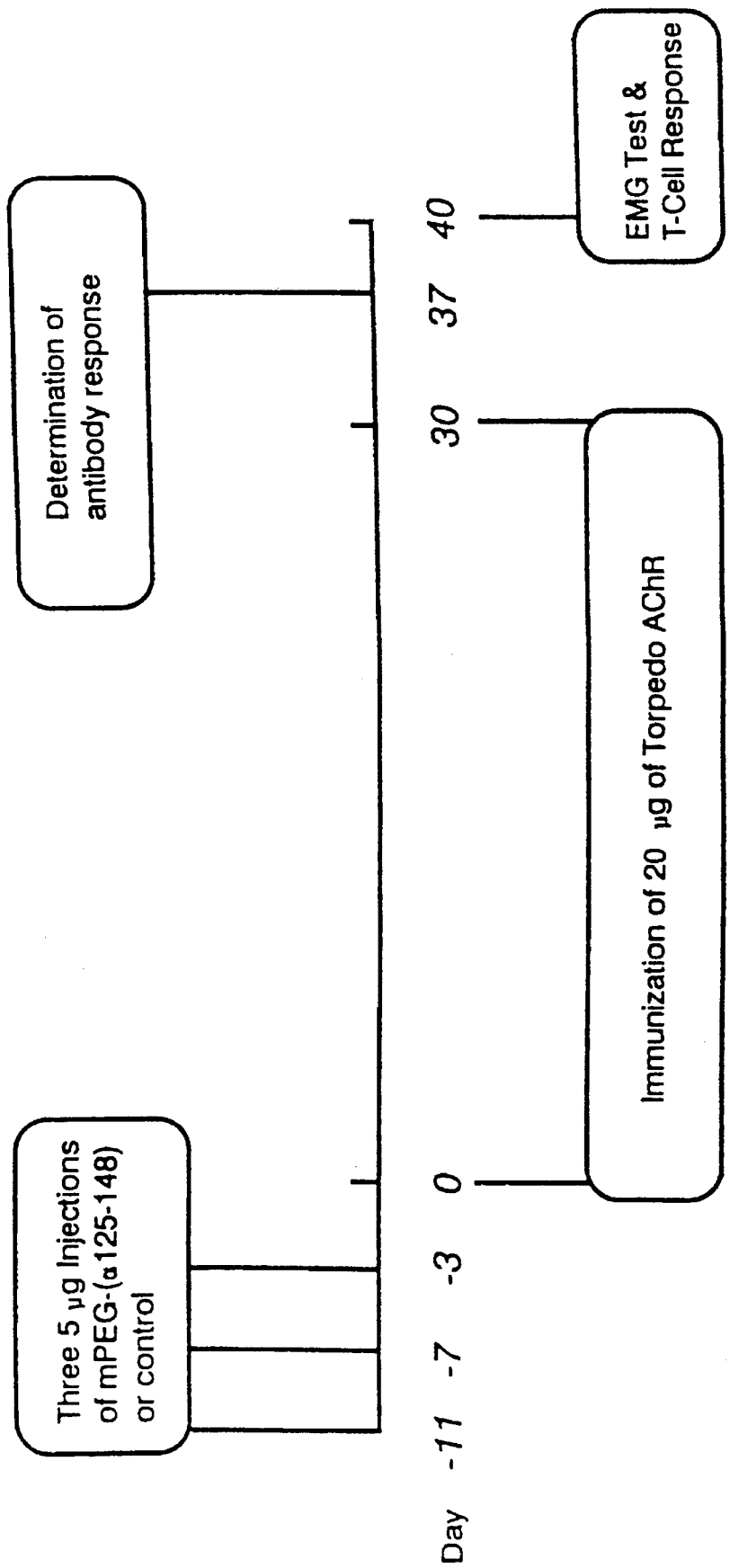
FIG. 5. Protocol for the intraperitoneal injections of C57/BL6 mice with mPEG-peptide conjugates (or the unconjugated peptide) and subsequent immunizations with whole Torpedo AChR.

Six weeks old C57/BL6 mice were purchased from Charles River Breeding Laboratories (Wilmington, Mass.). Preimmune sera were obtained from the mice for use as controls in subsequent antibody binding assays. After 2-weeks rest, the mice were divided into three groups which received, at eleven, seven and three days before immunization with AChR, an intraperitoneal injection (5 µg in 25 µl of PBS [0.15M NaCl in 0.01M sodium phosphate buffer, pH 7.2]) of either the mPEG-(α125-148) conjugate (Group 1), mPEG-nonsense peptide conjugate (Group 2) or unaltered free peptide α125-148 (Group 3) (FIG. 5). Then, on day 0, the mice were immunized subcutaneously in one hind footpad and intramuscularly in the same side shoulder with 20 µg of Torpedo AChR in 100 µl emulsion containing equal volumes of complete Freund's adjuvant and PBS. Thirty days later, the mice were immunized with a similar dose of the receptor in the opposite footpad and shoulder. On the 37th day, test bleeds were obtained from the mice for determination of the antibody titers. Electrophysiological studies were performed on the 38th and 39th days. Finally, the mice were sacrificed on the 40th day and lymph node cells were obtained for T cell studies.

Electrophysiological Studies

To document the electrophysiological evidence of EAMG, amplitudes of serial muscle action potentials were measured by electromyography (EMG) during the repetitive stimulation of the nerve in immunized mice, using the Mystro EMG system (TECA Corporation). A pair of wire electrodes were surgically implanted, encircling the sciatic nerve, two days before EMG. The nerve was stimulated through the implanted electrodes by 3 Hz trains of supramaximal electric current with a duration of 200 microseconds. The corresponding muscle action potentials were recorded with an electrode subcutaneously inserted over the gastrocnemius muscle. A reference electrode was placed at the ankle. Ether inhalation was used during the surgical and recording procedures. The amplitude of the initial evoked potential (P1) was compared to the third, fourth and fifth potentials, and the potential with the maximum amplitude deviation from the PI on either 3 Hz or 5 Hz stimulation was taken as Ps. The change of the amplitude was calculated as follows:

$$\text{Amplitude change \%} = \frac{(Ps - P1)}{P1} \times 100$$

Students' t-test was used to analyze the differences of amplitude changes between the two groups. A typical myasthenic response of a greater than 10% decrement was considered to constitute an electrophysiological evidence of EAMG. The frequency of electrophysiological EAMG was calculated in each group and analyzed by chi-square test.

Radioimmunoassay

One mg of the synthetic peptide was dissolved in 50 µl dimethylformamide and then diluted with PBS to 25 µg/ml. A solution of Torpedo AChR in PBS was prepared to contain 2.5 µg/ml. Aliquots (50 µl/well) of the peptide or AChR solutions were added to a 96-well microtiter plate (Falcon Micro Test III flexible assay plate, Becton Dickinson, Oxcard, Calif.) and the plates were incubated at room temperature overnight. After washing 3 times with PBS, the plates were blocked with 0.25% bovine serum albumin (BSA [bovine serum albumin]) in PBS (50 µl/well) at 37° C. for 90 minutes. The plates were washed again 5 times with PBS and to each well was added 50 µl of the serum from AChR-immunized mice, pre-diluted with PBS containing 0.10% BSA, and the plates were covered and allowed to stand at room temperature overnight. After 5 washes with PBS, 50 µl of rabbit IgG antibodies (2.5 µg/ml) against mouse IgG and IgM (Accurate Chemical Scientific Corporation, Westbury, N.Y.) was added to each well and the plates were incubated at 37° C. for 3 hours. The plates were then washed 5 times with PBS and $^{125}$I-labeled protein A ($2\times10^5$ cpm in 50 µl of PBS-0.1% BSA) was added to each well. The plates were incubated for 3 hours at room temperature, after which they were washed and the wells were cut out and counted for bound radioactivity. Pre-immune serum samples, obtained from the mice prior to any experimental treatments, were used as controls to correct for non-specific binding.

T Cell Proliferation Assay

Lymph node cells (LNC) were harvested from the AChR-primed mice of each group ten or eleven days after the last AChR immunization. The cells were suspended in RPMI 1640 (Gibco, Grand Island, N.Y.) containing 1% fresh autologous normal mouse serum. The number of viable cells was determined by vital staining with fluorescein diacetate. Viable LNC ($5\times10^5$ cells/well) were co-cultured in triplicate in flat bottom microtiter plates with various concentrations of mitogen, antigen or synthetic peptide in a final volume of 200 µl per well. The antigens used were Torpedo AChR peptides (α1-18 and α125-148, in the dose range 10–40 µg/ml), and Torpedo AChR (dose range, 1.5–6.0 µg/ml). Lysozyme and ovalbumin (100 µg/ml) and synthetic non-sense peptide (ESSGTGIESSGTGI, dose range 10–40 µg/ml) were used as negative controls. Concanavalin A (1 µg/ml) and lipopolysaccharide (500 µg/ml) were used as positive controls to monitor the viability of the cells. After incubation for 3 days at 37° C. in a humidified air/$CO_2$ (19:1) atmosphere, the cultures were pulsed (18 hr) with 1 µCi/well [$^3$H]-thymidine (Research Products International, Mount Prospect, Ill.) and then harvested on to glass microfiber filters (Whatman, Clinton, N.J.) for counting of radioactivity by liquid scintillation.

Example I

Synthesis of Peptide Conjugates Sequence ID Nos. 1–7

Figure 3:
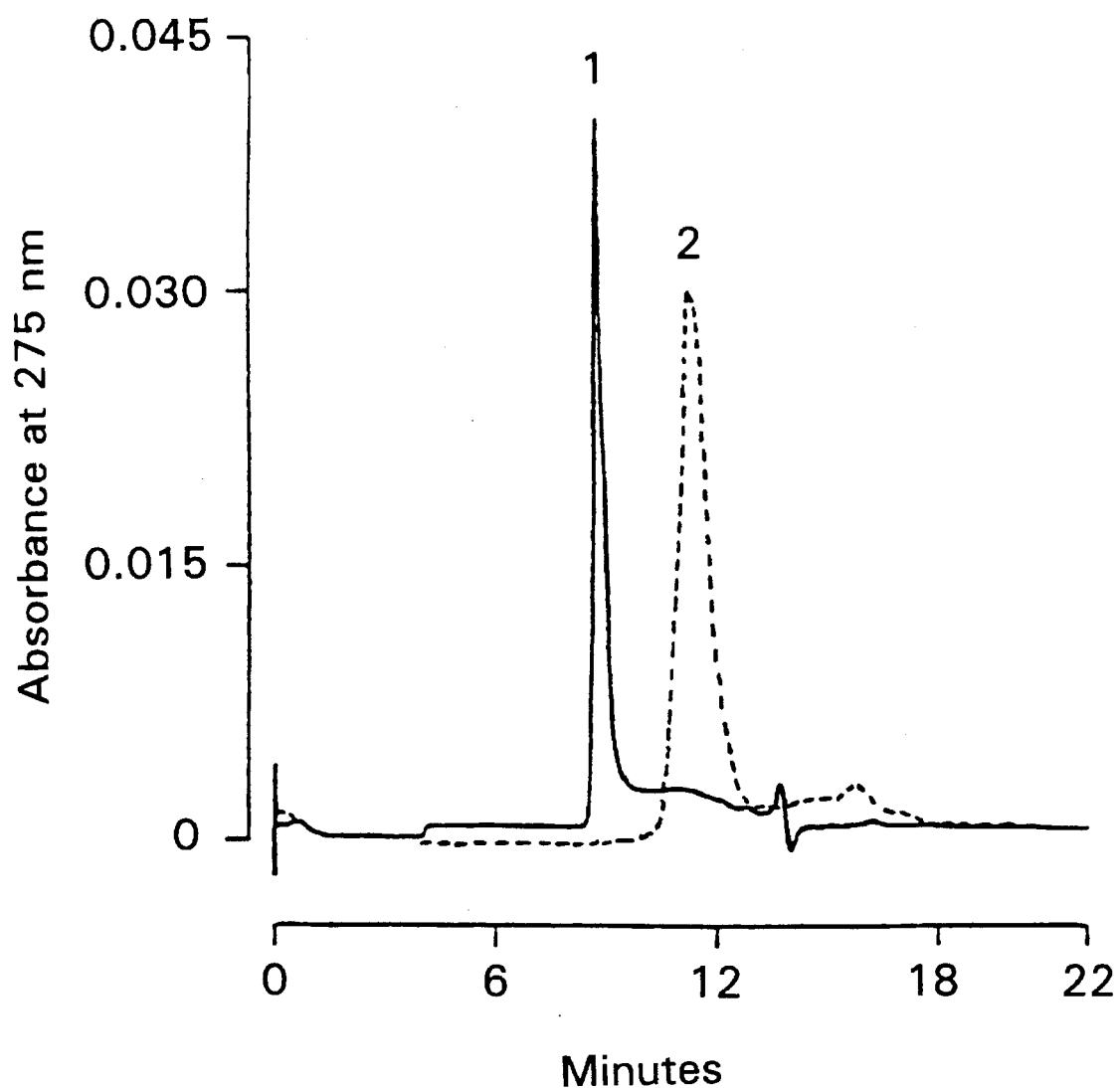
FIG. 3. An example of elution profiles of (1) the parent unconjugated peptide (peptide 5, FIG. 1) and (2) an mPEG-peptide conjugate in HPLC on a size exclusion column (Waters Protein Pak 60, 0.7×30 cm). The column was eluted with 0.2M ammonium bicarbonate containing 20% acetonitrile at 0.70 ml/min.

After purification, MPEG and PVA peptide conjugates were homogeneous molecular species and were confirmed to be free of the uncoupled peptide by HPLC on a size exclusion column (see FIG. 3, for an example). Furthermore, sequence analysis showed that the N-terminal was free in the uncoupled peptides and was completely blocked in the peptide conjugates. It should be noted that these peptides contained all possible amino acids. Furthermore, the attachment of MPEG or PVA to the N-terminal did not preclude the formation of intramolecular disulfide bonds in appropriate peptides (peptides 5 and 6 in FIG. 1, Sequence ID Nos. 5 and 6, respectively). It is, therefore, clear that this reaction should be universally applicable to coupling MPEG or PVA to any other synthetic peptide.

The present invention allows the preparation of peptide conjugates to mPEG or PVA by using a coupling reaction which ensured that the mPEG was linked to the peptide via its α-amino group on the N-terminal amino acid while the peptide is still attached to resin. This method provided a 1:1, tail-to-head (mPEG or PVA to peptide), monomeric conjugate of high purity. As noted previously, however, chemistries designed to mPEG derivatize the peptides of the invention at the carboxy terminus or at both the amino and carboxy termini are known to those of skill in the art and are expressly included within the scope of the present invention.

All the amino acid side chains within the conjugate, except for the N-terminal, remained unaltered and, because they were not attached to mPEG or PVA groups, they were capable of participating in immune recognition and epitope-specific immunoregulatory mechanisms. In contrast to the methods of the invention, mPEG-protein conjugates have been made by coupling mPEG to the protein, usually via ε-amino groups of lysine residues (Wei et al, 1981; Nordvall et al, 1986; Holford-Strevens et al, 1987; Jackson et al, 1987). This results in multiple substitutions on the protein surface and in modification of a number of lysine residues. The product would be expected to contain a mixture of molecular species of derivatives. The use of such compounds as tolerogens would potentially give rise to serious problems in reproducibility and efficacy, particularly in the recognition of individual epitopes by the immune system.

The general approach of epitope directed immunosuppression by well-defined tolerogenic peptide conjugates offers useful refined strategies for modulation of antibody responses to immunopathogenic sites on multi-determinant complex protein antigens. Because it provides a means to suppress the production of antibodies against the pathogenic epitopes, it should be applicable to autoantigens, alloantigens and allergens. mPEG itself does not seem to have any harmful or toxic effects in humans. Allergens conjugated to mPEG have already been safely administered to human subjects suffering from asthma (Mosbech et al, 1990) and honeybee venom allergy (Muller et al, 1987). Thus, the invention methods of mPEG or PVA conjugation to peptides should prove important, if not essential, for the employment of these peptide conjugates in specific tolerance to epitopes of protein antigens.

Example II

Specific Peptide Uses

Figure 6:
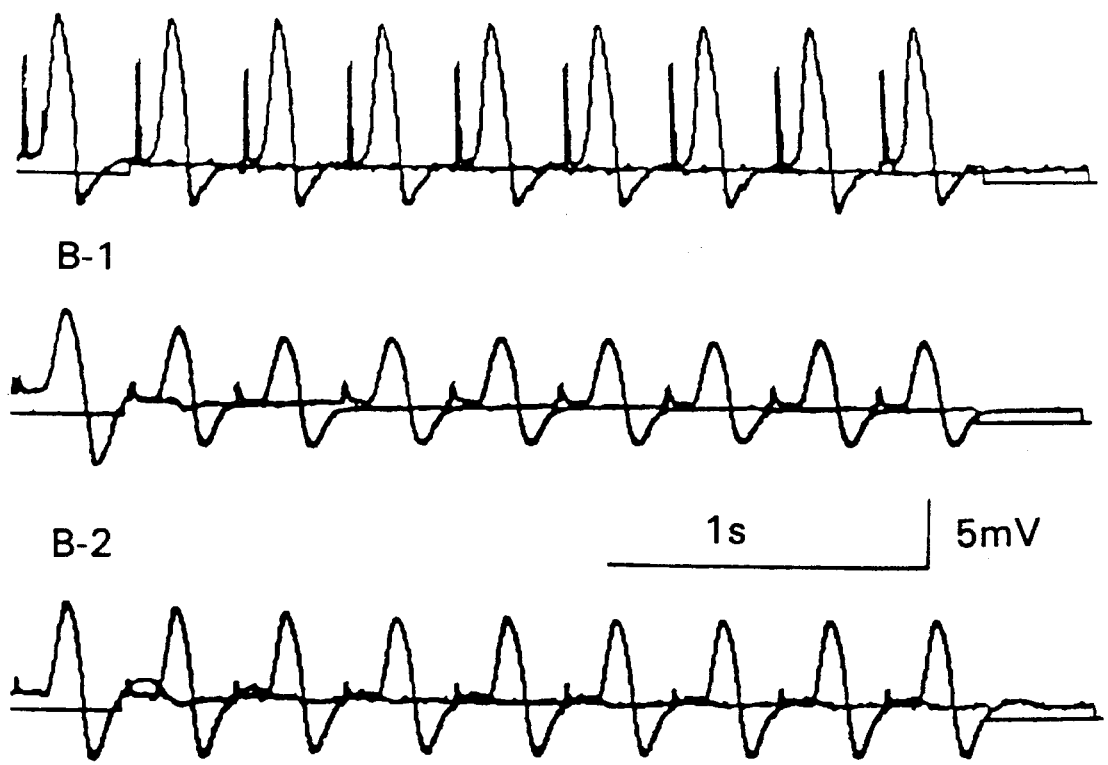
FIG. 6. An example of electrophysiological findings from a normal mouse and an EAMG-positive mouse. (A) EMG response of a normal mouse to a train of 3 Hz repetitive stimulation. (B1) a typical decremental response (−33%) in an EAMG-positive mouse. (B2) the decremental amplitude in B1 was substantially restored towards normal (−13%), 3 minutes after an intraperitoneal injection of 250 µg edrophonium chloride.
Figure 7:
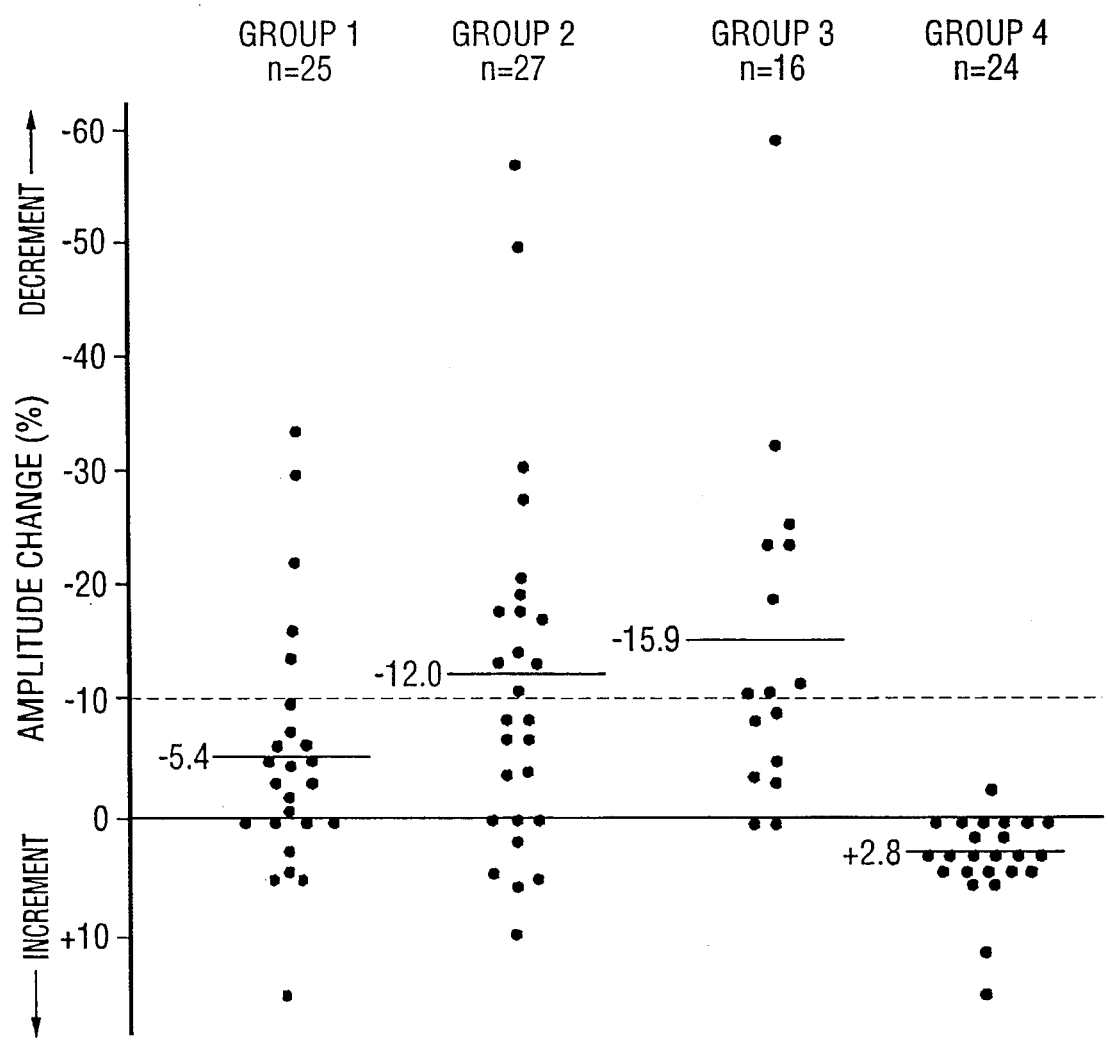
FIG. 7. Effects of prior administration of mPEG-($\alpha$125-148) on the development of electrophysiological EAMG after immunization with AChR (see FIG. 4). Note that in Group 1 mice, both the mean amplitude change and the proportion of mice showing greater than 10% decrement were smaller than Groups 2 or 3 ($p<0.05$), but greater than Group 4, mice ($p<0.05$), suggesting that the mPEG-($\alpha$125-148) conjugate suppresses development of electrophysiological EAMG but the suppression was incomplete.
Figure 8A:
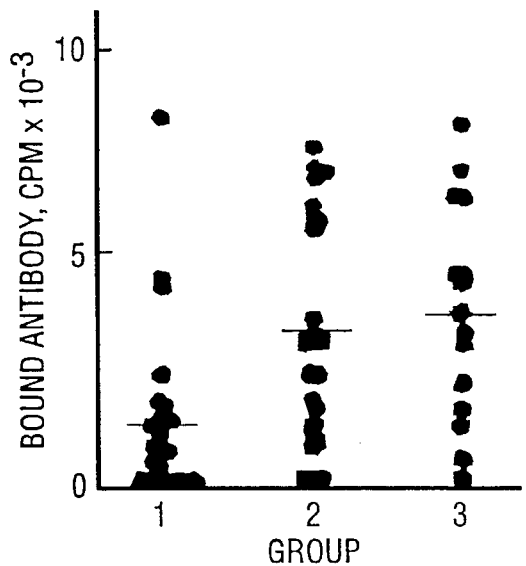
FIG. 8. Effects of pre-administration of mPEG-($\alpha$125-148) on the antibody response to immunization with AChR. The anti-AChR antisera from the three groups of mice (Groups 1–3) were studied for antibody binding to: (A)
Figure 8B:
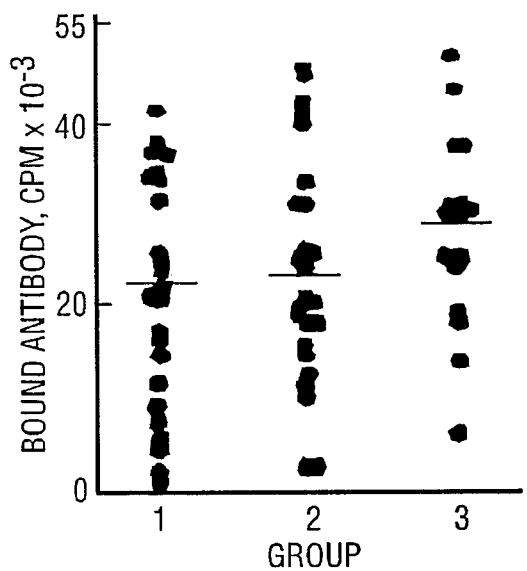
Figure 8C:
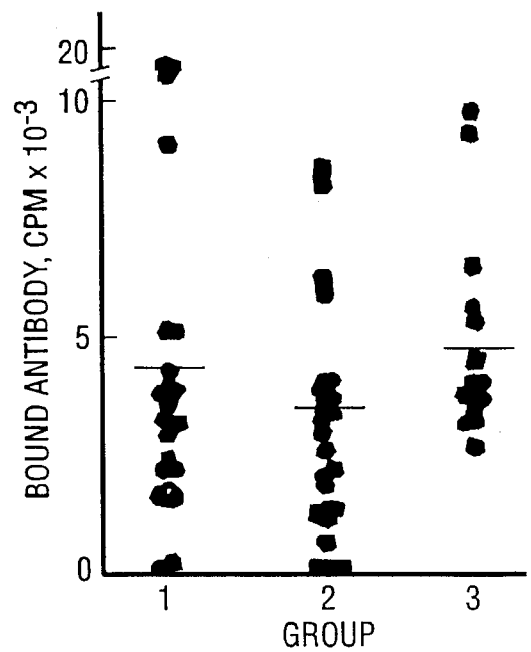
Figure 8D:
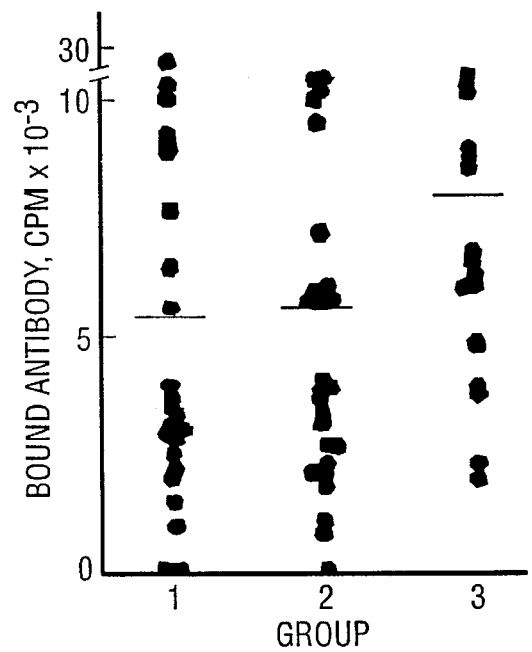

Effect of the mPEG-(α125-148) Conjugate on the Development of Electrophysiological EAMG Although some immunized mice showed muscle weakness, quantitative assessment of muscle weakness was difficult and, therefore, muscle action potentials were measured by EMG. Groups 1, 2 and 3 consisted of 25, 27 and 16 mice, respectively. Additional 24 mice received no intraperitoneal injections or immunizations (Group 4). The typical myasthenic decremental response was reversible upon intraperitoneal injection of 250 µg edrophonium chloride (FIG. 6). The results are summarized in FIG. 7. None of the mice in Group 4 showed a decremental response of the compound action potentials greater than 10%, and their mean amplitude change was +2.8% (i.e. 2.8 increment). Five (20%) of the 25 mice in Group 1 showed a decremental response greater than 10%, while 13 (48%) of the 27 mice of group 2 and 9 (56%) of the 16 mice of Group 3 developed the decremental response. The differences between Group 1 and groups 2 or 3 were statistically significant ($p<0.05$, chi-square test), but were insignificant between Group 2 and Group 3. The mean amplitude change in Group 1 was −5.4% (i.e. a 5.4% decrement), which was significantly smaller than that in Group 2 (−12.0%; $p<0.05$) or Group 3 (−15.9%; $p<0.05$), but greater than in Group 4 (+2.8%; $p<0.05$).

Effects of Pretreatment with mPEG-(α125-148) on the Antibody Response

The results of antibody binding to AChR and to selected regions of the e chain are summarized in FIG. 8. The antibodies bound to peptide α125-148 (FIG. 8A) were significantly decreased in the anti-AChR antisera from the group of mice which received the mPEG-(α125-148) conjugate (Group 1) prior to immunization with Torpedo AChR, whereas mice that had received mPEG-nonsense peptide (Group 2) or free α125-148 (Group 3) prior to AChR immunization exhibited no decrease in the antibodies directed against this region (FIG. 8A). Antibodies bound to whole Torpedo AChR (FIG. 8B), to peptide α45-60 (FIG. 8C) and to peptide α182-198 (FIG. 8D) were not significantly different among the three groups ($p>0.1$). To further confirm the epitope specific suppression of the antibody response, serum samples of the mice within each group were pooled and used in serial dilutions for determining the levels of antibodies against the region α125-148 (FIG. 9). The antiserum mixture from Group 1 [pretreated with mPEG-(α125-148)] had consistently lower amounts of antibody binding as compared to the antiserum mixture from Group 2 (pretreated with mPEG-Nonsense peptide) and group 3 (pretreated with unaltered free α125-148) and an additional group of mice without any treatment prior to the immunizations with AChR (Group 5). The antibody levels in Group 3 were consistently greater than the other two controls. Antibodies against peptide α125-148 were not detectable in Group 4 mice.

Effect of Pretreatment with mPEG-(α125-148) on the T Cell Proliferative Response The profiles of T-cell responses in EAMG-positive (pretreated with mPEG-Nonsense peptide) and EAMG-negative mice which had been treated with mPEG(α125148) were mapped with the synthetic overlapping peptides corresponding to the main extracellular domain (residues 1-210) of the a chain of Torpedo AChR. Lymph node cells from each group of mice were pooled separately based on their electrophysiological status for EAMG. The T cell proliferation profiles did not show meaningful differences among the groups regardless of their electrophysiological status (FIG. 10). The peptide recognition profile by AChR-primed T cells obtained here is in agreement with the profile previously reported for this mouse strain (Yokoi et al., 1987; Pachner et al., 1989).

Autoantibody-mediated mechanisms which have been demonstrated at the motor end plates in both EAMG and human myasthenia gravis include 1) pharmacological blockade of the acetylcholine binding site; 2) an increased rate of receptor degradation due to cross-linking of adjacent receptors, 3) an activation of the complement-mediated membrane lysis and 4) an alteration of the ion channel properties of the receptor (Ashizawa and Appel 1985). Previous studies with synthetic α125-148 and with overlapping synthetic peptides which comprised the entire extracellular domain of the α subunit of AChR have illustrated the pharmacological and immunological (Mulac-Jericevic et al., 1987) importance of this region. The sequence of the region α125-148 is highly conserved among species. It binds acetylcholine (McCormick and Atassi, 1984) and contains a universal binding region for long and short α-neurotoxins (Mulac-Jericevic and Atassi, 1987b; Ruan et al., 1990, 1991). Because of its direct involvement in the binding of acetylcholine and since the affinity of the antibodies to the receptor is several orders of magnitude higher than that of acetylcholine, the antibodies are capable of effectively blocking the acetylcholine binding site. Thus, the inventors reasoned that suppression of the antibody response to this region might alleviate the pharmacological blockade of the acetylcholine binding site, leading to the suppression of the development of EAMG.

It has been shown (Abuchowski et al., 1977; Lee and Sehon, 1977, 1978a; King et al., 1977, 1979; Davis et al., 1980; Sehon, 1989) that antibody responses to proteins can be modulated by protein-mPEG conjugates. It was not known, however, whether the approach may be used to obtain epitope-specific suppression of antibody responses to a preselected region of a protein. The results disclosed here demonstrate that injections of mice with mPEG-(α125-148) suppressed the development of electrophysiological EAMG induced by subsequent immunizations with whole Torpedo AChR, and this was accompanied by a suppression of autoantibody responses restricted to α125-148. These findings suggest that suppression of the antibody responses against this region rescued acetylcholine-binding sites on AChR from blockade by such antibodies. Other mechanisms may also play a role, however. Antibodies against the e subunit may be twice as likely to cross-link the adjacent receptors as antibodies against the other subunits, since the AChR is a pentamer consisting of two α subunits and one each of the β, γ and δ subunits. Because of this, and the fact that the region α125-148 is a major site of recognition by autoantibodies in EAMG, it is very likely that the population of antibodies directed against this region plays an important role in the development of EAMG through accelerated receptor degradation. Likewise, the decrease in this population of autoantibodies may lead to attenuation of the other pathophysiological mechanisms in EAMG.

The suppression of the electrophysiological EAMG was incomplete. Since the suppression of the antibody responses to region α125-148 was also incomplete, the remaining antibody activities against this region can partially account for the residual disease activity. Antibodies directed against other epitopes were not suppressed by the mPEG-(α125-148) conjugate and may also produce alterations of the synaptic transmission at the motor end plates through accelerated receptor degradation or by allosteric effects on the acetylcholine binding site and would thus have pathogenic activities.

Pretreatment with the mPEG-(α125-148) conjugate, followed by immunization with whole AChR, caused specific decrease of antibody responses directed against region α125-148, suggesting that the conjugate induces immunosuppression through the regulatory mechanisms involving specific epitope recognition. One of the first steps in immune regulation takes place in the presentation of epitopes to T cells by antigen presenting cells. It has been shown (Holford Strevens et al, 1987), in mice which had developed tolerance to native ovalbumin via intraperitoneal injections of an ovalbumin-mPEG conjugate, that the presentation of mPEG-modified antigen to T helper (Th) cells by peritoneal adherent cells was less efficient than the presentation of native antigen. However, since changes in the T-cell responses to α125-148 or to other AChR α-chain regions were not detected, it is unlikely that the presentation of mPEG-(α125-148) to Th cells is impaired. Another mechanism of tolerogenicity caused by the mPEG-(α125-148) conjugate may involve T suppressor (Ts) cells. A passive transfer of specific Ts cells activated by mPEG-antigen conjugates to syngeneic mice has been shown to cause antigen-specific immunosuppression in the recipient animals, suggesting that induction of antigen-specific Ts cells and release of suppressor lymphokines from these cells may play important roles (Lee et al., 1981; Mokashi et al., 1989; Sehon et al., 1989). Further experiments are needed to elucidate the role, if any, of Ts cells in the immunosuppression caused by the mPEG-peptide conjugate. Immunosuppression of antibody responses mediated by an mPEG-epitope conjugate may also operate at the level of T-B cell collaboration due to impairment of direct contact of the epitope-specific B cells with the conjugate resulting in central tolerance (Sehon and Lang, 1986). Differences might be expected, however, between the presentation and recognition of mPEG-protein conjugates and mPEG-peptide conjugates because of profound differences in their architecture.

In conclusion, these data suggest that mPEG-modified peptides corresponding to pathogenic autodeterminants of AChR may promise an effective immunospecific treatment for myasthenia gravis in the future. Furthermore, the general approach of epitope directed immunosuppression by well-defined tolerogenic mPEG-peptide conjugates offers useful refined strategies for modulation of antibody responses to immunopathogenic sites on multideterminant complex protein antigens. Because it provides a means to suppress the production of antibodies against the pathogenic epitopes, its application should not be restricted to autoantigens or alloantigens but should also be applicable to allergens. mPEG itself does not seem to have any harmful or toxic effects in humans.

EXAMPLE III

Clinical Applications of Epitope-Specific Suppression of Antibody Responses in Immune Diseases Methods of Treatment Allergens conjugated to mPEG have already been safely administered to human subjects suffering from asthma (Mosbech et al., 1990) and honeybee venom allergy (Muller et al., 1987) with therapeutic effects [these references as they pertain to methods of treatment of patients with undesirable immune responses, are specifically incorporated by reference herein]. Sehon (1988) has suggested new clinical applications of mPEG conjugates to arrest the progress of HIV infection to full blown acquired immunodeficiency syndrome (AIDS) in asymptomatic HIV-seropositive individuals. As opposed to the treatment protocols suggested in these prior art approaches which were limited by the masking of the epitopes by the tolerogenic polymer, the present invention exposes the epitope without masking or altering the conformation of a whole native polypeptide antigen (Sehon 1988).

A method of treatment for an immune disease such as myasthenia gravis, thus, is likely to follow closely these previous drug treatment protocols which used whole antigen. These approaches would be followed except that one would take advantage of the substantial improvement of there being no requirement to take into consideration the masking of the epitopes on the surface of the derivatized whole antigen. Thus, as in Sehon (1988) it was anticipated that the antigen binding capacity of antibodies directed against the allergen would be markedly reduced if not totally impaired as a result of conjugation of the allergen with mPEG. For that reason, in previous studies it was necessary to ensure the efficacy of the antibodies directed to the allergen by including a two-phase approach. In the first stage (immunosuppressive), a series of injections of tolerogenic mPEG conjugates of the antigen would be made for the induction of the immunosuppression as to the various epitopes represented on the whole antigen. In the second (effector) stage, a series of non-conjugated antigens would be injected, either with or without intermittent injections of the tolerogenic derivatives.

In the present invention, since there is no masking of the epitope by the tolerogenic polymer, there is no need to follow the injection of mPEG conjugated peptide epitopes with non-conjugated peptides. This represents a substantial improvement over the prior art approaches. These reagents will then be prepared into an immunotherapeutic reagent.

EXAMPLE IV

Immunoassays for disease detection and methods for screening potential reagents for efficacy in treatment of immune diseases The antigenic sites of proteins may either by continuous (i.e., occupy continuous segments of the protein chain) or discontinuous (i.e, formed by residues that may be distant in the sequence, but come into close spatial proximity in the three-dimensional structure) (Atassi, 1975; Atassi, 1978; Atassi and Smith, 1978). For a protein of an unknown antigenic structure, the two alternative site architectures should be anticipated. At the present time, any discontinuous antigenic sites, should they exist on AChR, cannot be investigated and mimicked without knowledge of the AChR three-dimensional structure, which is yet to be determined. In order to localize the continuous regions responsible for autoantibody binding on human AChR α-chain, the overlapping synthetic peptide approach was employed (Kazim and Atassi, 1980; Kazim and Atassi, 1982; Mulac-Jericevic et al. 1988; Mulac Jericevic and Atassi, 1987a; Mulac- Jericevic and Atassi, 1987b). This approach has enabled the localization of protein binding sites of diverse activities (Atassi, 1975; Atassi, 1978; Atassi, 1984; Atassi, 1988). The human AChR α-chain peptides were designed to cover the entire extracellular part (residues α1-210) of the subunit. Eighteen peptides were made (FIG. 11) that had a near uniform size of 16 or 17 residues and each peptide overlapped its adjacent neighbors by five residues (Mulac-Jericevic et al. 1988). In addition, a peptide (α262-276) corresponding to an extracellular connection between two transmembrane regions (Atassi et al. 1988) was investigated.

Immunoassays

It is proposed that the antigenic peptides or analogs of the same peptides of the invention will find utility as antigens in immunoassays for the detection of anti-peptide antigen-reactive antibodies. Turning first to immunoassays, in their most simple and direct sense, certain immunoassays of the invention include the various types of enzyme linked immunosorbent assays (ELISAs) known to the art. However, it will be readily appreciated that utility is not limited to such assays, and useful embodiments include RIAs and other non-enzyme linked antibody binding assays or procedures.

By way of example, in the ELISA assay, peptides incorporating the native antigen sequences (epitopes) are immobilized onto a selected surface, preferably a surface exhibiting a protein affinity such as the wells of a polystyrene microtiter plate. After washing to remove incompletely adsorbed material, one will desire to bind or coat a nonspecific protein such as bovine serum albumin (BSA) or casein onto the well that is known to be antigenically neutral with regard to the test antisera. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween. These added agents also tend to assist in the reduction of nonspecific background. The layered antisera is then allowed to incubate for from 2 to 4 hours, at temperatures preferably on the order of 25° to 27° C. Following incubation, the antisera-contacted surface is washed so as to remove non-immunocomplexed material. A preferred washing procedure includes washing with a solution such as PBS/Tween, or borate buffer.

Following formation of specific immunocomplexes between the test sample and the bound antigen, and subsequent washing, the occurrence and even amount of immunocomplex formation may be determined by subjecting same to a second antibody having specificity for the first. Of course, in that the test sample will typically be of human origin, the second antibody will preferably be an antibody having specificity in general for human Ig. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS-Tween).

After incubation with the second enzyme-tagged antibody, and subsequent to washing to remove unbound material, the amount of label is quantified by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer. It will, of course, be known to those skilled in the art that the chromatogenic protocol outlined above may be substituted by a radiological procedure such as the use of radioactive isotopes of iodine.

Screening Assays

An important aspect of the invention is the use of methods of the invention in screening assays for the identification of substances which may immunosuppress or otherwise modify or alter the undesirable immune response. The use of synthetically produced peptides (epitopes) is of particular benefit because the naturally occurring antigen may only be present in only small quantities and may difficult to purify from other immunogenic substances. Moreover, this allows one a ready source of a wide range of potential epitopes representing various regions on the surface of a polypeptide antigen.

The invention also provides access to human epitopes which may be difficult to produce otherwise if one is limited to collection of the native antigen from human tissues. Even so, by use of the human-derived epitopes in animal models, the sensitivity to various candidate substances can be first screened prior to human trials. The importance of this is quite significant in that it indicates that where one seeks to identify a compound, e.g., that may function to immunosuppress the disease in man, that one should employ human version of a particular epitope of a particular antigen for the screening assay.

The screening assays of the invention, in preferred embodiments, conveniently employ the animal model most directly mimicking the disease in humans. The battery of tests shown in Example II above for the disease model for myasthenia gravis are illustrative of the types of tests that can be used, e.g., electophysiological studies, radioimmunoassays, T-cell proliferations assays, etc.

In that most such screening assays in accordance with the invention will be designed to identify agents useful in inhibiting the undesirable immune response, preferred assays will typically employ the native antigen from which the peptides are derived in some aspect. Thus, it is preferred that a source of the native antigen be available.

There are believed to be a wide variety of embodiments which can be employed to determine the effect of a candidate substance such as a tolerogenic epitope-specific peptide on the immune disease of the invention, and the invention is not intended to be limited to any one such method. However, it will generally be desirable to employ a system wherein one can measure the ability of the candidate substance to immunosuppress the disease symptoms in the model.

One method employed by the inventors uses a mouse model for the screening of candidate epitopes capable of suppressing the experimental disease symptoms in mice. Similar studies have been accomplished using rat models of human allergy responses to Ra3. As mentioned previously, Grave's disease has well-known animal analogs.

In preferred assays, the admixture containing the tolerogenic peptide is injected at various intervals into a test subject and allowed to immunosuppress for a selected amount of time, and the resultant animals are tested for reduction of symptoms of the particular immune disease. Then, one simply measures the amount of each reduction in symptoms of the disease, e.g., versus a control to which no candidate substance has been injected. This measurement can be made at various time points where dosage rate data is desired. From this, one may determine the ability of the candidate substance to alter or modify the immune response of the disease.

EXAMPLE V

Detection and Diagnosis of Myasthenia Gravis

Blood Samples

Human blood samples were collected in heparinized tubes by venipuncture from patients with a confirmed diagnosis of MG, other neurological or autoimmune diseases and also from normal volunteers. The plasma was separated by centrifugation (3,000 rpm, 2° C., 10 min) and stored at 4° C. in 0.05% sodium azide. The samples were used within three weeks. Fifteen patients with MG were included in this study. The clinical diagnoses were confirmed by the presence of one or more of: (a) detectable anti-AChR antibody by a classical method (Vincent and Newson-Davis, 1985); (b) a positive edrophonium test; and (c) characteristic electrophysiological abnormalities at the motor endplates (Patten, 1978) (Table 1).

Fifteen control patients with disorders other than MG were included in the study. The diagnoses of these patients included: autoimmune polyneuropathy (one), chronic inflammatory demyelinating polyradiculoneuropathy (two), multiple sclerosis (one), optic neuritis (one), polymyositis (two), mononeuropathy multiplex due to vasculitis (one), motor axonopathy with anti-GM1 antibody (two), amyotrophic lateral sclerosis (one), Leukoencephalitis (one), Isaac-Merten Syndrome (one), arachnoiditis (one) and spinocerebellar degeneration (one). Normal subjects included ten males and five females between 22 and 49 years old.

Synthesis and Purification of the Peptides

Eighteen consecutive 16- or 17- residue peptides (FIG. 11), overlapping one another by 5 residues and spanning the entire extracellular part (residues α1-210) of human AChR α-chain (Mulac-Jericevic et al. 1988), were used to map the continuous autoantigenic (also often called myasthenogenic) regions on the extracellular part of the α-chain. In addition, a peptide corresponding to the inter-transmembrane region α262-276, Seq. ID No. 25, (Atassi et al. 1988) was studied (FIG. 11). The peptides were synthesized, purified and characterized as described (Mulac-Jericevic et al. 1988; Mulac-Jericevic and Atassi, 1987a; Mulac-Jericevic and Atassi, 1987b). Another eighteen overlapping peptide spanning the entire extracellular part (residues α1-210) of T. californica AChR α-chain were synthesized (Mulac-Jericevic et al. 1987) and used to raise anti-peptide antibodies and to test the coupling efficiency of the synthetic peptide to 96-well Co-Bind plates (covalent binding microtiter plate, Micro Membranes, Inc., N.J.).

Antibodies

Anti-peptide antibodies were raised in outbred mice by immunization in the hind footpads of 50 µg of synthetic peptide in 100 µl emulsion prepared from equal volumes of PBS and Freund's complete adjuvant. The immunizations were done on day 1, day 15, day 30 and day 45. Rabbit

TABLE 1[1]

| Patient Number | Age | Sex | MG Class | AchR-Ab (nM) | EMG | Edrophonium Test | Duration | Mediation | Thymus Histology |
|---|---|---|---|---|---|---|---|---|---|
| 1 | 74 | M | IIA | 155.0 | POS | POS | 5 (yrs) | PRED 10 mg qod | No thymectomy |
| 2 | 67 | M | IIC | 84.40 | POS | POS | 3 (yrs) | PYRID 30 mg tid CMP 100 mg pd PRED 50 mg qd | No thymectomy |
| 3 | 70 | F | I | 0.90 | NEG | POS | 7 (yrs) | NONE | No thymectomy |
| 4 | 35 | F | IIA | 8.18 | POS | POS | 19 (yrs) | PRED 50 mg gd | Hyperplasia |
| 5 | 34 | F | IIB | 6.28 | NEG | POS | 26 (yrs) | PYRID 60 mg qid | No thymectomy |
| 6 | 31 | F | IIA | 263.70 | POS | POS | 9 (yrs) | PYRID 60 mg bid | Hyperplasia |
| 7 | 65 | F | IIA | 39.75 | NEG | POS | 2 (yrs) | PYRID 120 mg qid | Thymoma |
| 8 | 67 | M | IIA | 1.84 | POS | POS | 18 (yrs) | PYRID 90 mg q4h | No thymectomy |
| 9 | 17 | F | IIA | 71.18 | POS | POS | 9 (yrs) | NONE | Hyperplasia |
| 10 | 33 | F | IIB | 4.30 | POS | POS | 11 (yrs) | PRED 10 mg qod | Hyperplasia |
| 11 | 61 | F | IIA | NEG | POS | POS | 8 (yrs) | PRED 15 mg qod | Histologic |
| 12 | 37 | F | IIA | 0.40 | POS | POS | 15 (yrs) | NONE | Histologic |
| 13 | 48 | F | IIA | 3.23 | POS | POS | 1 (yr) | PYRID 60 mg q4h | Thymoma |
| 14 | 25 | F | IIA | 52.00 | POS | POS | 2 (yrs) | PYRID 60 mg gid | Hyperplasia |
| 15 | 41 | M | N/A | NEG | POS | POS | 8 (yrs) | PYRID 60 mg qid | N/A |

[1]Abbreviations used in Table 1 are:
MG Class: Modified Osserman's Classification (Patten, 1978)
AchR-Ab: Normal range: <0.2 nM of binding sites for BGTX (0.2 nM = NORMAL MEAN VALUE + 3 STANDARD DEVIATIONS)
Medications: PRED: prednisone, PYRID: pyridostigmine bromide, CPM: cyclophosphamide All the medications were given orally. EMG: Electromyography with repetitive nerve stimulation (Patten, 1978) N/A: Not available immune IgG fractions with specificity against human IgG and human IgM and mouse IgG and IgM were obtained from DAKO Co. (DAKO-immunoglobulins a/s, Denmark) and Accurate Chemical Scientific Corp. (Westbury, N.Y.), respectively.

Binding of Autoantibodies to the Peptides 1.0 mg of peptide was dissolved in 5 µl of dimethylformamide and then diluted to 50 µg/ml with 0.15M NaCl in 0.01M sodium phosphate buffer, pH 7.2, containing 0.01% thimerosal (PBS). Aliquots of the peptide solution, were applied to wells of the 96-well Co-Bind plate. The plates were incubated at room temperature overnight with continuous gentle rocking. After washing three times with PBS, the wells were quenched (3 hrs., room temperature) with 0.2 ml of 1.0M glycine-NaOH, pH 7.2. After washing the wells three times with PBS, an aliquot (100 µl) of a 0.1% solution of casein in PBS were added to each well and the plates were incubated at 37° C. for 90 min to block the remaining reactive groups on the wells. The plates were then washed three times with PBS and incubated (37° C., 4 hrs) with 100 µl of plasma or mouse antiserum (1:200 or 1:500 dilution with PBS containing 0.1% casein). For binding to peptide α182-198, the plates were blocked with, and plasma were diluted in, 0.5% (instead of 0.1%) casein in PBS. After washing four times with PBS, the plates were incubated (4° C., overnight) with 100 µl of rabbit anti-human (IgG+IgM) or anti-mouse (IgG+IgM) (2.5 µg/ml) in PBS containing 0.1% casein. The plates were washed four times with PBS and incubated (3 hrs., room temperature) with $^{125}$I-labeled protein A ($2 \times 10^5$ cpm) in 100 µl of PBS-0.1% casein. After washing five times with PBS, bound radioactivity was removed from the wells, by the addition of 100 µl of 5% SDS in 0.2N NaOH. The plates were allowed to stand for 20 min at room temperature and the solutions were then transferred quantitatively to small test tubes for counting. This procedure was repeated three times, and the solutions in each case were added to the respective tubes. The samples were counted on a Beckman 4000 gamma counter. The radioactivity bound by three unrelated proteins (casein, cytochrome C and bovine serum albumin) and a nonsense peptide (ESSGTGIESSGTGI) (Atassi et al. 1987) were used as controls to correct for nonspecific binding. It should be noted that in other experiments, in which the plates were blocked and all dilutions were made with PBS containing human adult hemoglobin or bovine serum albumin, the non-specific binding was considerably higher than when casein was used.

Evaluation of the Coupling of the Synthetic Peptide to Co-Bind Plate

To confirm that the synthetic human AChR peptides can be coupled to Co-Bind plate, they were used to raise anti-peptide antibodies in mice. The peptides were bound onto the well of Co-Bind plates, followed by reaction with the respective anti-peptide antibody, pre-diluted 1:500 (v/v) with PBS/0.05% casein. The results (Table 2) showed that each peptide was able to bind to its own antibody. The results indicated that AChR peptides were in fact coupled to the wells.

TABLE 2

Binding of antibodies against human ACHR α chain peptides to the peptides on Co-Bind Plate[a]

| Peptide Binding | Seq. ID No. | Antibody Binding to immunizing Peptide (CPM)a |
|---|---|---|
| α1–16 | 7 | 78940 |
| α12–27 | 8 | 93038 |
| α23–38 | 9 | 71893 |
| α34–49 | 10 | 62360 |
| α45–60 | 11 | 82404 |
| α56–71 | 12 | 36038 |
| α67–82 | 13 | 22884 |
| α78–93 | 14 | 4433 |
| α89–104 | 15 | 29199 |
| α100–115 | 16 | 57717 |
| α111–126 | 17 | 51177 |
| α122–138 | 18 | 64218 |
| α134–150 | 19 | 52077 |
| α146–162 | 20 | 13649 |
| α158–174 | 21 | 14799 |
| α170–186 | 22 | 71323 |
| α182–198 | 23 | 68217 |
| α194–210 | 24 | 66804 |

[a] The CPM values have been corrected for nonspecific binding to casein (1.2–5% of the total binding to the peptides). The antisera were diluted 1:500 (v/v) with PBS/0.05% casein for this assay.

Binding of MG Autoantibodies to the Synthetic Peptides

The results of the binding profiles of autoantibodies from nine MG patients are summarized in FIG. 12. The figure also shows the binding profiles of plasma from nine normal controls. The results showed that the autoantibody recognition was directed essentially against four regions broadly localized within (but may not necessarily include all of) residues α10-30, α111-145 and α175-198 and, less frequently, residues α45-77. Not all the regions were necessarily recognized by any given MG plasma. For example in MG1 plasma, the autoantibody response to region α182-198, Seq. ID No. 23, was the most immunodominant, whereas in MG6 plasma, three of the regions were recognized and in MG7 all four regions were recognized. Other examples can be seen in FIG. 12. In general, the region residing within the consecutive overlapping peptide α170-186 (Seq. ID No. 22) and α182-198 (Seq. ID No. 23) was recognized by autoantibodies of all the individuals examined and was immunodominant in-most cases. Of the 19 peptides, peptides α182-198 (Seq. ID No. 23), α122-138 (Seq. ID No. 18), α111-126 (Seq. ID No. 17) and α12-27 (Seq. ID No. 8) were recognized by autoantibodies in 9, 8, 6 and 8 out of 9 individuals, respectively. The distribution of the responses to each one of these peptides in nine MG patients in summarized in FIG. 13 and compared to the binding distribution obtained with a similar number of normal, healthy individuals. For each one of these four peptides, the mean binding activity was clearly higher in MG plasma than in normal individuals (p<0.001 for α12-27, p<0.002 for α111-126, p<0,001 for α122-138 and p<0.001 for α182-198). However, because of the wide range of the binding distribution, none of these peptides could, by itself, serve as a specific marker for MG diagnosis (FIG. 13).

Binding of MG Autoantibodies to Mixture of Active Peptides

Since none of the active peptides could be relied upon for a clear diagnosis of MG, an equimolar mixture of the four most frequently active peptides (residues α12-27 [Seq. ID No. 8], α111-126 [Seq. ID No. 17], α122-138 [Seq. ID No.

18] and α182-198 [Seq. ID No. 23]) was used to determine autoantibodies in 15 MG plasma samples. The results are summarized in FIG. 14 and are compared with the binding levels obtained with 15 plasma samples from other neurological or autoimmune diseases and samples from normal individuals (supra). The 15 MG samples gave considerably higher amounts of antibody binding (mean net cpm, 5278±1398) than the binding obtained with the samples from the other neurological or autoimmune disease (mean net cpm, 956±652; p<<0.001) and the normal individuals (mean net cpm, 518±564; p<<0.001). The 15 MG samples clearly clustered at a higher level than the 15 samples from other neurological or autoimmune diseases and the 15 normal individuals, without any overlap with the two control groups. This is due to a complementary effect of the mixture on the binding activities of MG plasma. The MG samples which showed low binding activities for certain peptides had clearly higher binding activities for other peptides (FIG. 13). For example, MG2 had low binding activities for α111-126 and α182-198 (overlapping with control values), but showed clearly higher binding activities for α12-27 and α122-138 than any control plasma. The situation was similar for all MG plasma except for MG5. With the equimolar mixture of the four peptides, the low binding activities to certain peptides were complemented with the higher binding activities to other peptides in each MG plasma, while binding activities of control plasma were kept low.

Summary of the Continuous Antigenic Regions Recognized by Autoantibodies Against Human AChR in MG Patients The autoantibody binding profile to the human AChR peptides showed that four broad regions were generally recognized. However, except for peptide α182-198, not all the peptides within these four regions were positive with all the antisera. It Was shown previously that, in the immune responses to a multideterminant complex protein antigen, the response to each site is under separate Ir gene control (Okuda et al. 1979). Autoimmune responses to autoantigenic sites are also under genetic control (Yokota et al. 1980; David and Atassi, 1982). The results with the MG plasma indicate that the autoimmune responses to the individual antigenic sites are each under genetic control. Because of this complication, no universal single peptide was found which will bind with anti-AChR autoantibodies in all MG plasma. Therefore, four peptides (α12-27, α111-126, α122-138 and α182-198) were selected because each was able to bind antibodies in the majority of the plasma samples investigated. The cocktail of these peptides enabled the detection of the autoantibodies in all 15 MG plasma samples whereas control plasma from 15 patients with other neurological or autoimmune disorders as well as 15 normal healthy individuals were essentially negative showing that no significant amounts of antibodies against these regions of AChR were present in these individuals.

Using these 18 human AChR peptides, the peptide T-cell recognition profiles were determined for autoimmune T-cell lines that were prepared from peripheral blood lymphocytes of several MG patients by passage in vitro with an equimolar mixture of the peptides (Oshima et al. 1990). It was found that the profiles of the peptides recognized by the autoimmune T cells were different among the five T-cell lines, consistent with genetic control operating at the level of the individual recognition sites. In the present work, plasma samples were obtained from two of the MG patients (MG4 and MG6) for whom the T-cell recognition profile was determined (Oshima et al. 1990). It will, therefore, be valuable to compare, for each of these patients, his/her autoimmune antibody and T-cell recognition profiles. The comparison is summarized schematically in FIG. 15. The autoimmune T-cell line from MG4 recognized four peptides, only one of which (peptide α23-38) was also recognized by autoantibodies. Two T-cell recognition regions, α1-17 and α89-104, shared an overlap with antibody recognition regions within residues α12-27 and α100-115, respectively. It is very likely that when the precise boundaries of the respective autoimmune T- and B-cell recognition sites are determined, the overlaps between these recognition features will be more extensive (Atassi et al. 1987). It should be noted that the overlapping peptide strategy (Kazim and Atassi, 1980; Kazim and Atassi, 1982) is not expected to give the boundaries of the autorecognition sites but rather to localize the maximal continuous regions within which these sites would reside.

At any rate, one T-cell auto-determinant within region α146-162 (Seq. ID No. 20) was exclusively a T-cell recognition feature, since no autoantibodies were directed to it in this individual. The T-cell line from MG6 recognized three auto-determinants, two of which (α111-126 and α182-198, Seq. ID Nos. 17 and 23, respectively) coincided completely with regions recognized by autoantibodies while the third (α146-162) shared an overlap with the autoantibody binding region within residues α134-150 (Seq. ID No. 19). It is evident, therefore, that in given individuals, autoantibodies and autoimmune T-cells may recognize similar sites, but there are in addition sites that are recognized only by antibodies and sites that are recognized only by T cells. This is consistent with previous findings on T- and B-cell recognition of proteins in foreign hosts (for review, see ref. (Atassi, 1984) and in human allorecognition of class II MHC molecules (Lindstrom et al. 1976). The results reported here and previously with autoimmune T-cells suggest that the pathogenesis of this autoimmune disease is variable at the molecular-cellular level.

By using the overlapping peptide strategy employed here, the present inventors have mapped the regions of a-neurotoxin (both BgTX and cobratoxin) binding on the extracellular part of the α-subunits of Torpedo californica (Mulac-Jericevic and Atassi, 1987a; Mulac-Jericevic and Atassi, 1987b) and human (Mulac-Jericevic et al. 1988) AChR. A major toxin binding region was found (Mulac-Jericevic et al. 1988; Mulac-Jericevic and Atassi, 1987a; Mulac-Jericevic and Atassi, 1987b) to reside within the peptide α122-138 and two minor regions occur within peptides α34-49 and α194-210. The results reported here show that peptide α122-138 also contains an autoantigenic region in most MG sera. The binding activity of this region with autoantibody and with α-neurotoxin would explain the false negatives obtained with the method that relies on the precipitation by the autoantisera of the 125I-labeled BgTX-AChR complex. The region α122-138 carries contact residues of the acetylcholine binding sites (McCormick and Atassi, 1984). The present finding that autoantibodies also bind to this region provides a molecular explanation for the dysfunction of AChR in MG. The present work, in addition to localizing the continuous regions of autoantibody recognition from which the molecular basis for the dysfunction in MG may be better understood, identifies a cocktail of peptides that may be employed successfully to reduce an ambiguous diagnosis.

Thus, utilizing the materials and methods of the present the present inventors have localized the major continuous auto-antigenic regions on the extracellular part of the α-chain of human AChR that are recognized by autoantibodies in MG patients. One of these regions contained contact residues of the acetylcholine binding site. This has provided a molecular explanation for the dysfunction of AChR in the autoimmune disease. Furthermore, the results permitted comparison of the autoantibody recognition profile with autoimmune T-cell recognition regions on human AChR in the same donor. By using an equimolar mixture of the most frequently active peptides, it has been possible to detect the autoantibodies in all the MG sera examined. This peptide mixture provides a molecular basis for reliable diagnosis of the disease.

REFERENCES CITED

The following references to the extent that they provide procedural details supplementary to those set forth herein, are specifically incorporated herein by reference.

Abuchowski, A., van Es., T., Palczuk, N. C. and Davis, F. F., *J. Biol. Chem.* 252:3578 (1977).

Anzinger and Mutter, *Polymer Bulletin* 6:595 (1982).

Ashizawa, T. and Appel, S. H., *Springer Sem Immunopathol.* 8:177–196 (1985).

Atassi, M. Z., *Immunochemistry* 12:423–438 (1975).

Atassi, M. Z., *Immunochemistry* 15:909–936 (1978).

Atassi, M. Z., *Europ. J. Biochem.* 145:1–20 (1984).

Atassi, H. and Atassi, M. Z., *FEBS Lett.* 188:96 (1985).

Atassi, H. and Atassi, M. Z., *Europ. J. Immunol.* 16:229 (1986).

Atassi, M. Z. and Manshouri, T., *J. Prot. Chem.*, in press (1992).

Atassi, M. Z., Manshouri, T. and Sakata, S., *Proc. Natl. Acad. Sci. USA* 88: 3613 (1991).

Atassi, M. Z., Manshouri, T. and Yokoi, T., *FEBS Letters* 228:295–300 (1988).

Atassi, M. Z., Mulac-Jericevic, B., Yokoi, T. and Manshouri, T., *Federation Proc.* 46:2538–2547 (1987).

Atassi, M. Z., Ruan, J. H., Jinnai, K., Oshima, M. and Ashizawa, T., *Proc. Ntl. Acad. Sci. USA* (1999), submitted.

Atassi, M. Z. and Saplin, B. J., *Biochemistry* 7:688–698 (1968).

Atassi, M. Z. and Smith, J. A., *Immunochemistry* 15:609–610 (1978).

Becker and Bayer, *J. Am. Chem. Soc.* 101:239 (1979).

Changeux, J. P., Devillers-Thiery, A. and Chemouilli, P., *Science* 225:1335–1345 (1984).

David, C. S. and Atassi, M. Z., *Adv. Exp. Med. Biol.* 150:97–126 (1982).

Davis, F. F., Abuchowski, A., van Es, T., Palczuk, N. C., Savoca, K., Chen, R. H.-L. and Pyatuk, P., In *"Biochemical Polymers: Polymeric Materials and Pharmaceuticals for Biomedical Use"* (E. P. Goldberg and A., Nakajima, Eds.), pp. 441–452. Academic Press, New York, 1980.

Falpius, B. W., Miskin, R. and Reich, E., *Proc. Natl. Acad. Sci.* 77:4326–4330 (1980).

Finer-Moore, J. and Stroud, R. M., *Proc. Natl. Acad. Sci.* 81:155–159 (1984).

Froehner, S. C. and Rafto, M. Z. *Biochemistry* 18:301–307 (1979).

Guy, H. R., *Biophys. J.* 45:249–261 (1984).

Holford-Strevens, V., Jackson, C.-J. C., Charlton, J., Akiyama, K. A., Lang, G. M., Carter, B. G. and Sehon, A. H., *Cellular Immunology* 104:245–254 (1987).

Hucho, F., *Eur. J. Biochem.* 158:211–226 (1986).

Jackson, C.-J. C., Charlton, J. L., Kuzminski, K., Lang, G. M. and Sehon, A. H., *Analytical Biochemistry* 165:114–127 (1987).

Kaiser, E., Colescott, R. L., Bassinger, C. D. and Look, D. T., *Anal. Biochem.* 34:595–598 (1970).

Karlin, A., *Cell surface and neuronal function* (Edited by Colman, C. W., Poste, G. and Nicolson, G. L.), pp. 191–260. Elsevier/North-Holland Biomedical Press, New York (1980).

Kazim, A. L. and Atassi, M. Z., *Biochem. J.* 191:261–264 (1980).

Kazim, A. L. and Atassi, M. Z., *Biochem. J.* 203:201–208 (1982).

King, T. P., Kochoumian, L. and Chiroazzi, N., *J. Exp. Med.* 149:424 (1979).

King, T. P., Kochoumian, L. and Lichtenstein, L. M., *Arch. Biochem. Biophys.* 178:442 (1977).

Kita, et al., *Drug Design Delivery* 6:157 (1990).

Kurisaki, et al. *Europ. J. Immunol.* 16:236 (1986).

Kyte and Doolittle, *J. Molec. Biol.* 157:105 (1982).

Laemmli, U., *Nature (London)* 266:680–685 (1970).

Lee, C. Y., *Adv. Cytopharmacol.* 3:1–16 (1979).

Lee, W. Y. and Sehon, A. H., *Nature (London)* 267:618 (1977).

Lee, W. Y. and Sehon, A. H., *Arch. Allergy Appl. Immunol.* 56:159 (1978a).

Lee, W. Y. and Sehon, A. H., *Arch. Allergy Appl. Immunol.* 56:193 (1978b).

Lee, W. Y., Sehon, A. H. and Akerblom, E., *Int. Arch. Allergy Appl. Immunol.* 64:100 (1981).

Lefvert, A. K., Bergstrom, K., Matell, G., Osterman, P. O. and Pirskanen, R., *J. Neurol. Neurosurg. and Psych.* 41:394–403 (1978).

Lindstrom, J. M., Seybold, M. E., Lennon, V. A., Whittingham, S. and Duane, D. D., *Neurology* 26:1054–1059 (1976).

McCormick, D. J. and Atassi, M. Z., *Biochem. J.* 224:9950–10000 (1984).

Mokashi, S., Holford-Strevens, V., Sterrantino, G. and Jackson, C. J., *Immunol. Lett.* 23:95–102 (1989).

Moore, H. H. and Raftery, M. A., *Biochemistry* 18:1862–1867 (1979).

Mosbech, H., Dirksen, A., Dreborg, S., Frlund, L., Heinig, J. H., Svendsen, U. G., Sborg, M., Taudorf, E. and Weeke, B., *Allergy* 45:142–150 (1990).

Mulac-Jericevic, B. and Atassi, M. Z., *J. Prot. Chem.* 6:365–373 (1987).

Mulac-Jericevic, B. and Atassi, M. Z., *Biochem. J.* 248:847–852 (1987a).

Mulac-Jericevic, B. and Atassi, M. Z., *J. Prot. Chem.* 6:365–373 (1987b).

Mulac-Jericevic, B., Kurisaki, J. and Atassi, M. Z., *Proc. Natl. Acad. Sci. USA* 84:3633–3637 (1987).

Mulac-Jericevic, B., Manshouri, T., Yokoi, T. and Atassi, M. Z., *J. Prot. Chem.* 7:173–177 (1988).

Muller, U., Rabson, A. R., Bischof, M., Lomnitzer, R., Dreborg, S. and Lanner, A., *J. Allergy Clin. Immunol.* 80:252–261 (1987).

Nishimura, et al., *Life Sciences* 33:1467 (1983).

Noda, M., Furutani, Y., Takahashi, H., Toyosato, M., Tanabe, T., Shimizu, S., Kikyotani, S., Kayano, T., Hirose, T., Inoyama, S. and Numa, S., *NATURE* 305:818–823 (1983).

Noda, M., Takahashi, H., Tanabe, T., Toyosato, M., Furutani, Y., Hirose, T., Asai, M., Inayama, S., Miyata, T. and Numa, S., *Nature (London)* 299:793–797 (1982).

Nordvall, S. L., Uhlin, T., Ohman, S., Bjorkander, J., Malling, H-J., Week, B., Dreborg, S., Lanner, A. and Einarsson, R., *Allergy* 41, 89–94 (1986).

Oger, J., Kaufman, R. and Berry, K., *Canadian J. Neurol. Sci.* 14:297–302 (1987).

Okuda, K., Twining, S., David, C. S. and Atassi, M. Z., *J. Immunol.* 123:182–188 (1979).

Oshima, M., Ashizawa, T., Pollack, M. Z. and Atassi, M. Z., *Eur. J. Immunol.* 20:2563–2569 (1990).

Pachner, A. P., Kantor, F. S., Mulac-Jericevic, B. and Atassi, M. Z., *Immunology Letters* 20:199–204 (1989)

Patten, B. M., *Muscle. Nerve.* 1:190–205 (1978).

Ruan, K.-H., Spurlino, J., Quiocho, F. A. and Atassi, M. Z., *Proc. Natl. Acad. Sci. USA* 87:6156–6160 (1990).

Ruan, K. H., Stiles, B. G. and Atassi, M. Z., *Biochem. J.* 274:849–854 (1991).

Sakakibara, S., Shimonishi, Y., Kishida, T., Okada, M. and Sugihara, H., *Bull. Chem. Soc.* Japan 40:2164 (1967).

Sartore, et al., *Appl. Biochem. Biotechnol.* 27:55 (1991).

Sehon, A. H., *Adv. Exp. Med. Biol.* 251:341–351 (1989).

Sehon, A. H., *In immunobiology of proteins and peptides V-Vaccines:Mechanisms, Design, and Applications*, ed. M. Z. Atassi, pp. 341, plenum Press, New York (1988).

Sehon, A. H. and Lang, G. M., *In Mediators of Immune Regulation and immunotherapy* (S. K. Singhal and T. L. Delovitch, Eds.) PP. 190–203, Elsevier, New York (1986)

Sobel, A., Weber, M. and Changeux, J. P., *Eur. J. Biochem.* 80:215–224 (1977).

Tzartos, S. J. and Changeux, J. P., *EMBO. J.* 2:381–387 (1983).

Ueyama, et al., *Polymer J.* 17:721 (1985).

Vincent, A. and Newson-Davis, J., *J. Neurol. Neurosurg. and Psych.* 48:1246–1252 (1985).

Wei, S. I., Wei, C. W., Lee, W. Y., Filion, L. G., Sehon, A. H. and Akerblom, E., *Int. Arch. Allergy Appl. Immunol.* 64:84–99 (1981).

Yokoi, T., Mulac-Jericevic, B., Kurisaki, J. T. and Atassi, M. Z., *Europ. J. Immunol.* 17:1697–1702 (1987).

Yokota, S., Davis, C. S. and Atassi, M. Z., *Mol. Immunol.* 17:1079–1082 (1980).

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. For example, it will be understood that one may synthesize the peptides of the invention or one may obtain peptide fragments which are either wholly or partially a fragment of a native antigen or a recombinant derivative of such. Additionally, while the amino acid sequence selected for a given peptide will typically occur as such in the native antigen, it will be understood that one may choose to substitute similar hydropathic amino acids and that the peptide may contain non-linear portions (i.e., such a peptide may represent a discontinuous epitope) of a given antigen, alloantigen or allergen. Similarly, one may wish to add amino acid residues to either one or both termini of the epitope proper which amino acid residues are not relevant to the specificity of the epitope but otherwise facilitate its use or ease of purification, for instance. It is also understood that the tolerogenic polymer molecule may be coupled either to the N-terminal $\alpha$-$NH_2$ group or to the C-terminal carboxyl group or, in certain cases, to both termini. All such modifications are intended to be included within the scope of the appended claims.

What is claimed is:

1. A method for the detection of human acetylcholine receptor (AChR) autoantibodies in patient serum samples, said autoantibodies being associated with the disease myasthenia gravis, said method comprising the following steps:
   (a) obtaining a serum sample from a patient suspected of having myasthenia gravis or being at risk for the development of said disease;
   (b) contacting said serum sample with a composition comprising peptides having the following sequences: SEQ ID NOS. 8, 17, 18, and 23;
   (c) washing said samples to remove nonspecifically bound antibodies; and,
   (d) detecting peptide-autoantibody complex formation;
   wherein detection of said peptide-autoantibody complexes indicates the presence of human acetylcholine receptor autoantibodies.

2. The method of claim 1 wherein the serum sample is a blood sample.

3. The method of claim 1 wherein the risk of having the disease is heightened by a family history of the disease.

4. The method of claim 1 wherein a measure of suspicion of the patient's having, or risk of developing said disease involves a pre-test.

5. The method of claim 4 wherein said pre-test is an edrophonium assay.

6. The method of claim 4 wherein said pre-test is a test of electrophysiological abnormalities at motor endplates of the patient.

7. A peptide composition useful for the detection of human acetylcholine receptor (AChR) autoantibodies, which are associated with the disease myasthenia gravis, in patient serum samples comprising peptides having the following sequences: SEQ ID NOS. 8, 17, 18, and 23.

8. A diagnostic kit for the detection of human acetylcholine receptor (AChR) autoantibodies in patient serum samples, said autoantibodies being associated with the disease myasthenia gravis, said kit comprising peptides having the following sequences: SEQ ID NOS. 8, 17, 18, and 23.

9. The diagnostic kit of claim 8, wherein the immunodetection reagent is a radiolabeled reagent.

10. The diagnostic kit of claim 9, wherein the radiolabeled reagent comprises radioactive iodine.

11. The diagnostic kit of claim 8, wherein the immunodetection reagent is an enzyme-linked immunosorbent assay reagent.

* * * * *